United States Patent [19]

Takematsu et al.

[11] 4,358,309

[45] Nov. 9, 1982

[54] UREA DERIVATIVES AND HIGHLY SELECTIVE HERBICIDAL COMPOSITIONS CONTAINING THE SAME

[75] Inventors: Tetsuo Takematsu, Utsunomiya; Masaki Takeuchi, Ohmiya; Masanori Okada, Niiza; Hiroshi Sugiyama; Yasushi Murakami, both of Tokyo, all of Japan

[73] Assignee: Chugai Seiyaku Kabushiki Kaisha, Tokyo, Japan

[21] Appl. No.: 247,711

[22] Filed: Mar. 26, 1981

[30] Foreign Application Priority Data

Apr. 17, 1980 [JP] Japan .................... 55-49575
May 16, 1980 [JP] Japan .................... 55-64038

[51] Int. Cl.³ .................... C07C 69/76; C07C 127/19; A01N 9/20
[52] U.S. Cl. .................... 71/120; 564/52; 260/453 RW
[58] Field of Search .................... 564/52; 260/453 RW; 71/120

[56] References Cited

U.S. PATENT DOCUMENTS

| | | | |
|---|---|---|---|
| 3,903,156 | 9/1975 | Teach | 71/120 X |
| 4,129,436 | 12/1978 | Takemoto et al. | 71/120 |
| 4,144,049 | 3/1979 | Yoshida et al. | 71/120 |
| 4,221,817 | 9/1980 | Tenne | 71/120 X |
| 4,249,938 | 2/1981 | Takemoto et al. | 564/52 X |
| 4,260,411 | 4/1981 | Yoshida et al. | 564/52 X |
| 4,263,219 | 4/1981 | Fujita et al. | 71/120 X |
| 4,294,986 | 10/1981 | Spatz et al. | 564/52 |

FOREIGN PATENT DOCUMENTS

| | | | |
|---|---|---|---|
| 503459 | 4/1971 | Switzerland | 71/120 |
| 528861 | 11/1972 | Switzerland | 71/120 |
| 532891 | 3/1973 | Switzerland | 71/120 |

*Primary Examiner*—Thomas A. Waltz
*Attorney, Agent, or Firm*—Browdy and Neimark

[57] ABSTRACT

There are provided novel urea derivatives of the general formula

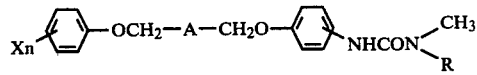

wherein X, n, A and R are defined in the description; processes for preparing the derivatives and herbicidal composition containing as active ingredient the derivative. The derivatives have highly selective herbicidal activities.

19 Claims, No Drawings

UREA DERIVATIVES AND HIGHLY SELECTIVE HERBICIDAL COMPOSITIONS CONTAINING THE SAME

This invention relates to a urea derivative of the formula

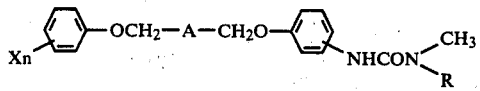
(I)

wherein X is a halogen, an alkyl or trifluoromethyl, n is an integer of from 0 to 3, provided that when n is 2 or 3, X may be different to each other; A is

or —C≡C—, wherein

is in trans form; and R is methyl or methoxy. This invention also relates to a process for preparing the urea derivative defined above, and to a herbicidal composition containing the same.

The inventors had studied in order to develop a herbicidal composition having highly selective herbicidal activity, namely, having low phytotoxicity to useful plants such as crops, and high toxicity to weeds, and found a group of compounds represented by the formula (I) above. The inventors confirmed that the compounds exhibit high selectivity between the useful plants and weeds and have very low toxicity for humans, animals, especially livestocks, fish, shellfish and the like, and finally completed this invention.

Various urea series herbicidal compounds which contain in the molecule, the same moiety as that of the compounds of this invention are known. However, it is also known that such conventional urea herbicidal compounds have relatively poor selectivity between the useful plants and weeds. Although many attempts have been made, no significant improvement has been obtained.

Examples of the commercially available urea series compounds are N'-N-chlorophenyl-N,N-dimethylurea (monuron), N'-3,4-dichlorophenyl-N,N'-dimethylurea (diuron), and N'-3,4-dichlorophenyl-N-methoxy-N-methylurea (linuron). Although these types of compounds have high herbicidal activity against weeds, they exhibit at the same time, high phytotoxicity to useful plants. Therefore, in practical application, the conditions for application and particular useful plants and weeds must be carefully selected, and the use thereof is limited to a certain extent.

On the other hand, various compounds of triazine series are known for use as a herbicidal agent. However, it is generally recognized that the triazine compounds, like the urea compounds described hereinbefore, have low selectivity. For example, 2,4-bis(ethylamino)-6-methylthio-1,3,5-triazine (simetryne) is taken through roots of plants at a relatively slow rate in comparison with other types of triazine compounds, and it has been broadly used in order to control broadleaf weeds. However, the practical application of the compound is limited, especially when it is applied to paddy field, as the rice plant is often injured under water flooded conditions and at an elevated temperature. So, the compound must be used carefully on paddy fields.

In contrast, the compounds represented by the formula (I) of this invention exhibit, as shown in Experiments hereinbelow, no or slight phytotoxicity to useful plants, and a very strong herbicidal activity against harmful weeds, regardless of the particular application conditions and particular plants and weeds to be treated. The compounds of this invention have very high selectivity between crops and weeds.

The compounds of this invention represented by the formula (I) are novel and can be prepared by the various processes described hereunder.

(1) The compounds represented by the formula (I) are prepared by reacting a compound of the formula (II)

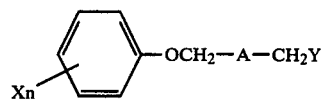
(II)

wherein X, A and n are as defined above and Y is a halogen, with a urea derivative represented by the formula (III)

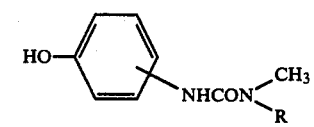
(III)

wherein R is as defined above. The reaction is carried out in an appropriate solvent with aid of a proper acid acceptor to give the object compound in a high yield.

The solvents useful in this reaction include hydrocarbons such as benzene, toluene and the like; ethers such as diethyl ether, tetrahydrofuran, dioxane and the like; alcohols such as methanol, ethanol and the like; hydrocarbon halides such as chloroform; esters such as ethyl acetate; and other organic solvents such as dimethylformamide and the like; and mixture thereof. If desired, water or an aqueous mixture of one or more organic solvents can be used.

The acid acceptors useful in this reaction include, for example, organic compounds such as pyridine, triethylamine and the like; and inorganic compounds such as sodium hydroxide, potassium hydroxide, sodium carbonate, sodium hydride and the like.

The reaction is usually carried out at room temperature, but may be carried out under cooling or under heating depending on the particular reactants, solvents or acid acceptors used. The reaction is completed usually within 1–8 hours. After completion of the reaction, the product is recovered from the reaction mixture by the conventional isolation and/or purification technique.

The compounds of the formula (I) can also be prepared by the following process (2).

(2) The compounds are prepared by reacting a phenol derivative represented by the formula (IV)

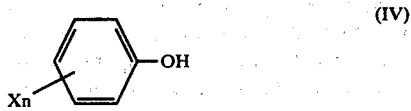  (IV)

wherein X and n are as defined above, with a urea derivative represented by the formula (V)

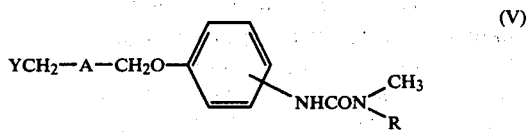  (V)

wherein Y, A and R are as defined above. The reaction is carried out in a solvent and with aid of an acid acceptor to give the object compound in a high yield.

The solvents and acid acceptors useful in the reaction (2) include those which can be used in the reaction (1). Although the reaction proceeds at room temperature, it may be carried out under cooling or under heating, depending on the particular reactants, solvents or acid acceptors to be used. The reaction is completed within 1–8 hours under suitable reaction conditions. Upon completion of the reaction, the product is separated and purified in any suitable conventional way.

(3) The compounds of the formula (I) can also be prepared with a high yield by reacting an aniline derivative represented by the formula (VI)

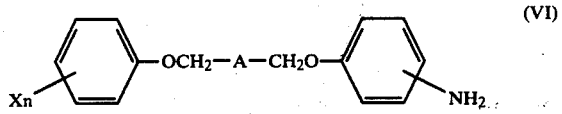  (VI)

wherein X, A and n are as defined above, with a carbomoyl chloride derivative of the formula (VII)

  (VII)

wherein Y and R are as defined above.

The reaction is carried out in a solvent with aid of an acid acceptor. The solvents and acid acceptors useful in this reaction are those specified for the reaction (1).

Although the reaction proceeds at room temperature, it may be carried out under cooling or under heating, depending on the particular reactants, solvents and acid acceptors to be used. The reaction is completed within 1–8 hours under suitable conditions. The product is separated and purified in any suitable way.

(4) Further, the compounds of the formula (I) can be prepared with a high yield by reacting a phenylisocyanate derivative of the formula (VIII)

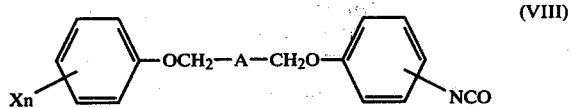  (VIII)

wherein A, X and n are as defined above, with an amine derivative of the formula (IX)

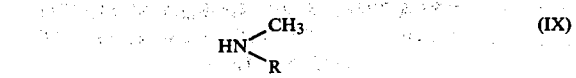  (IX)

wherein R is as defined above.

This reaction is carried out using an inert solvent and an acid acceptor such as those exemplified in the explanation for the reaction (1).

Although the reaction proceeds at room temperature, good results may be given by cooling or heating the reaction system, depending on particular reactants and solvent to be used. The reaction is usually completed within 1–8 hours, although the reaction time varies broadly, depending on particular conditions applied. The product is separated and purified by any suitable conventional technique.

(5) The compounds of this invention represented by the formula (I) wherein R is methoxy can be prepared with a high yield of methylating a urea derivative represented by the formula (X)

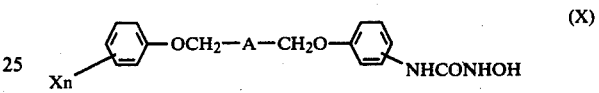  (X)

wherein X, A and n are as defined above.

Examples of the methylating agent useful in this invention are dimethylsulfate, methyl iodide, diazomethane and the like.

The reaction conditions such as reaction temperature, time and the like vary broadly, depending on the particular solvents, reaction promoters, methylating agents, etc., but satisfactory results are obtained by applying the conventional methylating technique to this reaction.

The preparation of various compounds of this invention is further illustrated by the following Preparations.

PREPARATION 1

4-(4-Chloro-2-methylphenoxy)-2-trans-butenyl chloride (2.3 g) was added to a solution of potassium hydroxide (0.78 g) and N'-4-hydroxyphenyl-N,N-dimethylurea (1.8 g) in ethanol (30 ml), and the mixture was stirred at 50°–60° C. for 4 hours and then diluted with water and extracted with ethyl acetate. The solvent was evaporated from the extract under reduced pressure and the residue was recrystallized from ethanol to give 3.1 g of N'-4-[4-(4-chloro-2-methylphenoxy)-2-trans-butenyloxy]-phenyl-N-methyl-N-methoxyurea. (m.p.: 122°–123° C.) (Compound No. 32)

Analysis: Calcd. for $C_{20}H_{23}ClN_2O_3$ (molecular weight: 374.87): C, 64.08; H, 6.18; N, 7.47 (%). Found: C, 64.29; H, 6.23; N, 7.49 (%)

PREPARATION 2

4-(2,6-Dimethylphenoxy)-2-trans-butenyl chloride (2.1 g) was added to a solution of potassium hydroxide (0.78 g) and N'-3-hydroxyphenyl-N-methyl-N-methoxyurea (2.0 g) in ethanol (40 ml) and the mixture was subjected to reaction by heating it at 60°–70° C. for 5 hours while stirring. After completion of the reaction, the reaction mixture was diluted with water and extracted with ethyl acetate. The solvent was evaporated under reduced pressure. The residual oily product was chromatographed using a column filled with silica gel and chloroform as an eluent to isolate the product. The fractions containing the product were combined and the solvent was evaporated to give as an oily substance 3.0 g of N'-3-[4-(2,6-dimethylphenoxy)-2-trans-butenyloxy]-phenyl-N-methyl-N-methoxyurea. (Compound No. 106)

Analysis: Calcd. for $C_{21}H_{26}N_2O_4$ (molecular weight: 370.45): C, 68.09; H, 7.07; N, 7.56 (%). Found: C, 68.33; H, 7.15; N, 7.40 (%)

PREPARATION 3

N'-3-(4-Chloro-2-trans-butenyloxy)-phenyl-N-methyl-N-methoxyurea (2.9 g) was added to a solution of sodium hydroxide (0.6 g) and 2,4-dichlorophenol (1.4 g) in methanol (50 ml) and the mixture was reacted by heating it at 50° C. for 4 hours while stirring. After completion of the reaction, the reaction mixture was diluted with water and extracted with ethyl acetate. The solvent was evaporated from the extract under reduced pressure and the resulting residue was recrystallized from ethyl acetate/n-hexane to give 3.2 g of N'-3-[4-(2,4-dichlorophenoxy)-2-trans-butenyloxy]-phenyl-N-methyl-N-methoxyurea. (m.p.: 91°–92° C.) (Compound No. 98)

Analysis: Calcd. for $C_{19}H_{20}Cl_2N_2O_4$ (molecular weight: 411.28): C, 55.49; H, 4.90; N, 6.81 (%). Found: C, 55.53; H, 4.90; N, 6.70 (%)

PREPARATION 4

A solution of 4-[4-(4-chlorophenoxy)-2-trans-butenyloxy]-aniline (2.7 g) and triethylamine (1.2 g) in tetrahydrofuran (30 ml) was cooled with ice, and to the solution was added slowly dimethyl-carbamoly chloride (1.3 g). After completion of the addition, the mixture was stirred under cooling with ice for 30 minutes, and then at room temperature for 2 hours. The resulting triethylamine hydrochloride was removed by filtration, and the solvent was evaporated from the filtrate under reduced pressure. The resulting risidue was recrystallized from diethyl ether to give 3.0 g of N'-4-[4-(4-chlorophenoxy)-2-trans-butenyloxy]-phenyl-N,N-dimethylurea. (m.p.: 144°–145° C.) (Compound No. 4)

Analysis: Calcd. for $C_{19}H_{21}ClN_2O_3$ (molecular weight: 360.84): C, 63.24; H, 5.88; N, 7.76 (%). Found: C, 63.18; H, 5.92; N, 7.88 (%)

PREPARATION 5

3-[4-(4-Chloro-2-methylphenoxy)-2-trans-butenyloxy]phenyl-isocyanate (3.3 g) was dissolved in tetrahydrofuran (30 ml) and a 50% dimethylamine aqueous solution (1 g) was added dropwise to the solution while stirring and cooling with ice. After completion of the addition, the mixture was stirred for 30 minutes while stirring under cooling with ice, and then stirred at room temperature for an additional 2 hours. The solvent was evaporated under reduced pressure and the resulting residue was recrystallized from ethyl acetate/n-hexane to give 2.9 g of N'-3-[4-(4-chloro-2-methylphnoxy)-2-transbutenyloxy]-phenyl-N,N-dimethylurea. (m.p.: 116°–118° C.) (Compound No. 80)

Analysis: Calcd. for $C_{20}H_{23}ClN_2O_3$ (molecular weight: 374.87): C, 64.08; H, 6.18; N, 7.47 (%). Found: C, 63.97; H, 6.21; N, 7.51 (%)

PREPARATION 6

A solution of 3-[4-(2,4-dimethylphenoxy)2-trans-butenyloxy]-phenylisocyanate (3.1 g) in methylene chloride (10 ml) was added dropwise to an aqueous solution of hydroxylamine hydrochloride (0.5 g) and sodium hydroxide (0.5 g) while stirring and cooling with ice. After completion of the addition, the stirring was continued for an additional 30 minutes under the same condition, and then at room temperature for 2 hours. The reaction mixture was then diluted with water and the precipitate was recovered by filtration and dried. The product was dissolved in benzene methanol (1:1) (50 ml), and 1.0 N aqueous sodium hydroxide (1 ml) and dimethylsulfate (1.3 g) were added dropwise to the solution while stirring and cooling with ice. After completion of the addition, the mixture was stirred for an additional 30 minutes under the same conditions, and then at room temperature for 2 hours. The reaction mixture was diluted with water and extracted with benzene, and the solvent was evaporated. The resulting residue was recrystallized from ethyl acetate/n-hexane to give 2.6 g of N'-3-[4-(2,4-dimethylphenoxy)-2-trans-butenyloxy]phenyl-N-methyl-N-methoxyurea. (m.p.: 84.5°–85° C.) (Compound No. 104)

Analysis: Calcd. for $C_{21}H_{26}N_2O_4$ (molecular weight: 370.45): C, 68.09; H, 7.07; N, 7.56 (%). Found: C, 68.33; H, 7.15; N, 7.40 (%)

PREPARATION 7

4-(3-Methyl-4-chlorophenoxy)-2-butynyl chloride (2.29 g) was added to a solution of N'-4-hydroxyphenyl-N-methyl-N-methoxyurea (1.96 g) and potassium hydroxide (0.65 g) in ethanol (30 ml), and the mixture was stirred at 60° C. for 5 hours to react the reactants. After completion of the reaction, the ethanol was evaporated under reduced pressure, and the resulting residue was diluted with water and extracted with benzene. The benzene layer was washed with 5% aqueous sodium hydroxide and then with water, and dried over sodium sulfate. After removing the sodium sulfate by filtration, the benzene was evaporated under reduced pressure to give an oily product. Recrystallization of the oily product from benzene/n-hexane gave 2.4 g of N'-4-[4-(3-methyl-4-chlorophenoxy)-2-butynyloxy]-phenyl-N-methyl-N-methoxyurea. (m.p.: 79.5°–80° C.) (Compound No. 166)

Analysis: Calcd. for $C_{20}H_{21}ClN_2O_4$ (molecular weight: 388.84): C, 61.77; H, 5.44; N, 7.20 (%). Found: C, 61.55; H, 5.32; N, 7.19 (%)

PREPARATION 8

3,4-Dichlorophenol (1.9 g) was added to a solution of sodium hydride (0.29 g) in dimethylformamide (20 ml), and then N'-4-(4-chloro-2-butynyloxy)-phenyl-N,N-dimethylurea (2.67 g) was added to the mixture followed by stirring it at 50° C. for 5 hours. After completion of the reaction, the reaction mixture was poured into water (50 ml) and the separated oily phase was extracted with benzene. The benzene layer extract was washed with 5% aqueous sodium hydroxide and then with water, and dried over sodium sulfate. After removing the sodium sulfate by filtration, the benzene was evaporated under reduced pressure. The residue was recrystallized from ethyl acetate/n-hexane to give 2.36 g of N'-4-[4-(3,4-dichlorophenoxy)-2-butynyloxy]-phenyl-N,N-dimethylurea. (m.p.: 113°–114° C.) (Compound No. 131)

Analysis: Calcd. for $C_{19}H_{18}Cl_2N_2O_3$ (molecular weight: 393.26): C, 58.02; H, 4.61; N, 7.12 (%). Found: C, 58.15; H, 4.70; N, 7.07 (%)

PREPARATION 9

4-[4-(3,5-Dimethylphenoxy)-2-butynyloxy]aniline (2.81 g) and triethylamine (1.4 ml) were dissolved in tetrahydrofuran (30 ml). To the solution was added dropwise a solution of N,N-dimethylcarbamoly chloride (1.07 g) in tetrahydrofuran (15 ml) while stirring and cooling with ice-water. After completion of the addition, the mixture was stirred under cooling for 30 minutes, and at room temperature for 2 hours to complete the intended reaction. After completion of the reaction, the tetrahydrofuran was evaporated under reduced pressure and water was added to the residue to give crystals which were recovered by filtration and dried. The crystals were recrystallized from ethyl acetate/n-hexane to give 2.95 g of N'-4-[4-(3,5-dimethylphenoxy)-2-butynyloxy]-phenyl-N,N-dimethylurea. (m.p.: 145°–146° C.) (Compound No. 138)

Analysis: Calcd. for $C_{21}H_{24}N_2O_3$ (molecular weight: 352.42): C, 71.56; H, 6.86; N, 7.94 (%). Found: C, 71.38; H, 6.87; N, 7.99 (%)

PREPARATION 10

O,N-Dimethylhydroxylamine hydrochloride (1.17 g) and triethylamine (1.68 g) were dissolved in chloroform (50 ml). To this solution another solution of 3-[4-(3,4-dimethylphenoxy)-2-butynyloxy]phenylisocyanate (3 g) in chloroform (20 ml) was added dropwise while stirring and cooling with ice water. After completion of the addition, the stirring was continued under cooling for 30 minutes, and then at room temperature for 5 hours to complete the intended reaction. After addition of water, the reaction mixture was extracted with chloroform. The chloroform layer was separated, dried over sodium sulfate, and, after removing the sodium sulfate, evaporated under reduced pressure to remove the chloroform. The residue was recrystallized from benzene/n-hexane to give 2.65 g of N'-3-[4-(3,4-dimethylphenoxy)-2-butynyloxy]phenyl-N-methyl-N-methoxyurea. (m.p.: 93.5°–94.5° C.) (Compound No. 201)

Analysis: Calcd. for $C_{21}H_{24}N_2O_4$ (molecular weight: 368.42): C, 68.45; H, 6.56; N, 7.60 (%). Found: C, 68.44; H, 6.66; N, 7.53 (%)

PREPARATION 11

A solution of 3-[4-(3,4-dimethylphenoxy)-2-butynyloxy]phenyl-isocyanate (3 g) in methylene chloride (10 ml) was added dropwise, while stirring and cooling with ice, to a solution of hydroxylamine hydrochloride (0.8 g) and sodium hydroxide (0.5 g) in water (10 ml). After completion of the addition, the reaction mixture was stirred under cooling for 30 minutes, and then at room temperature for 2 hours to complete the intended reaction. Then, water was added to the reaction mixture to form a precipitate which was recovered by filtration and dried.

The thus obtained solid hydroxyurea derivative was dissolved in benzene/methanol (1:1) (50 ml), and to the solution were added 10 N aqueous sodium hydroxide (1 ml) and dimethyl sulfate (1.3 g) while stirring and cooling with ice. After completion of the addition, the mixture was stirred under cooling for 30 minutes and then at room temperature for 2 hours to complete the reaction. The, water was added to the reaction mixture and the resulting precipitate was extracted with benzene. The benzene layer was separated and evaporated to remove benzene. The residue was recrystallized from benzene/n-hexane to give 1.8 g of N'-3-[4-(3,4-dimethylphenoxy)-2-butynyloxy]-phenyl-N-methyl-N-methoxyurea. (m.p.: 93°–94° C.) (Compound No. 201)

When the compound was subjected to mixed examination with the product of Preparation 10, no drop in the mixed melting point was observed.

Typical compounds represented by the formula (I) of this invention which were prepared in the same way as in the previous Examples are listed in the following Table 1. It should be understood that the compounds in Table 1 are shown for illustrative purpose, not for limitation.

In Table 1, figures of from 2 to 6 in the column for "Substituent X" represent the position on benzene nucleus, and "m" and "p" in the column entitled "Binding Position" represent meta- and para- positions on the other benzene nucleus with respect to the substituent

The NMR spectra of the products given as oily substances by conventional isolation and purification technique are shown in Table 2.

Further, Et, Pr, Bu and Am in Table 1 represent $-C_2H_5$, $-C_3H_7$, $-C_4H_9$ and $-C_5H_{11}$, respectively.

The compound number assigned in the previous Preparations and in Tables below will be used in Examples and Experiments hereunder.

TABLE 1

| Compound No. | Substituents X | | | | | R | A | Bonding position | Melting point (°C.) |
|---|---|---|---|---|---|---|---|---|---|
| | 2 | 3 | 4 | 5 | 6 | | | | |
| 1 | — | — | — | — | — | CH₃ | —C≡C— | p | 138–139 |
| 2 | Cl | — | — | — | — | CH₃ | —C≡C— | p | 125–127 |
| 3 | — | Cl | — | — | — | CH₃ | —C≡C— | p | 129.5–131.5 |
| 4 | — | — | Cl | — | — | CH₃ | —C≡C— | p | 144–145 |
| 5 | — | — | Br | — | — | CH₃ | —C≡C— | p | 154–156 |

TABLE 1-continued

| Compound No. | Substituents X 2 | 3 | 4 | 5 | 6 | R | A | Bonding position | Melting point (°C.) |
|---|---|---|---|---|---|---|---|---|---|
| 6 | F | — | — | — | — | CH₃ | —C=C— | p | 113.5–114.5 |
| 7 | — | F | — | — | — | CH₃ | —C=C— | p | 146–146.5 |
| 8 | — | — | F | — | — | CH₃ | —C=C— | p | 139–139.5 |
| 9 | CH₃ | — | — | — | — | CH₃ | —C=C— | p | 129–130.5 |
| 10 | — | CH₃ | — | — | — | CH₃ | —C=C— | p | 124–126.5 |
| 11 | — | — | CH₃ | — | — | CH₃ | —C=C— | p | 156–157 |
| 12 | — | — | Et | — | — | CH₃ | —C=C— | p | 144–145 |
| 13 | — | — | n-Pr | — | — | CH₃ | —C=C— | p | 134–135 |
| 14 | — | — | i-Pr | — | — | CH₃ | —C=C— | p | 142–143.5 |
| 15 | — | — | sec-Bu | — | — | CH₃ | —C=C— | p | 109–110 |
| 16 | — | — | t-Bu | — | — | CH₃ | —C=C— | p | 158–159 |
| 17 | — | — | sec-Am | — | — | CH₃ | —C=C— | p | 93–95 |
| 18 | — | — | t-Am | — | — | CH₃ | —C=C— | p | 102–103 |
| 19 | — | CF₃ | — | — | — | CH₃ | —C=C— | p | 127–128 |
| 20 | Cl | Cl | — | — | — | CH₃ | —C=C— | p | 125.5–127.5 |
| 21 | Cl | — | Cl | — | — | CH₃ | —C=C— | p | 121–122.5 |
| 22 | Cl | — | — | Cl | — | CH₃ | —C=C— | p | 115–116 |
| 23 | Cl | — | — | — | Cl | CH₃ | —C=C— | p | 116–117.5 |
| 24 | — | Cl | Cl | — | — | CH₃ | —C=C— | p | 157–159 |
| 25 | — | Cl | — | Cl | — | CH₃ | —C=C— | p | 142–143 |

TABLE 1-continued

| Compound No. | Substituents X 2 | 3 | 4 | 5 | 6 | R | A | Bonding position | Melting point (°C.) |
|---|---|---|---|---|---|---|---|---|---|
| 26 | CH$_3$ | CH$_3$ | — | — | — | CH$_3$ | —C=C— | p | 135–137 |
| 27 | CH$_3$ | — | CH$_3$ | — | — | CH$_3$ | —C=C— | p | 133–134 |
| 28 | CH$_3$ | — | — | CH$_3$ | — | CH$_3$ | —C=C— | p | 137–139 |
| 29 | CH$_3$ | — | — | — | CH$_3$ | CH$_3$ | —C=C— | p | 137–139 |
| 30 | — | CH$_3$ | CH$_3$ | — | — | CH$_3$ | —C=C— | p | 146 |
| 31 | — | CH$_3$ | — | CH$_3$ | — | CH$_3$ | —C=C— | p | 126–128 |
| 32 | CH$_3$ | — | Cl | — | — | CH$_3$ | —C=C— | p | 122–123 |
| 33 | Cl | — | — | — | CH$_3$ | CH$_3$ | —C=C— | p | 121–122 |
| 34 | — | CH$_3$ | Cl | — | — | CH$_3$ | —C=C— | p | 138 |
| 35 | Cl | — | t-Bu | — | — | CH$_3$ | —C=C— | p | 124–125 |
| 36 | Cl | — | Cl | Cl | — | CH$_3$ | —C=C— | p | 141–142 |
| 37 | Cl | — | Cl | — | Cl | CH$_3$ | —C=C— | p | 128–129 |
| 38 | CH$_3$ | — | CH$_3$ | — | CH$_3$ | CH$_3$ | —C=C— | p | 110–111 |
| 39 | Cl | — | Cl | — | CH$_3$ | CH$_3$ | —C=C— | p | 133–134 |
| 40 | — | CH$_3$ | Cl | CH$_3$ | — | CH$_3$ | —C=C— | p | 153.5–154.5 |
| 41 | — | — | — | — | — | OCH$_3$ | —C=C— | p | 90–91 |
| 42 | Cl | — | — | — | — | OCH$_3$ | —C=C— | p | 114–115 |
| 43 | — | Cl | — | — | — | OCH$_3$ | —C=C— | p | 78–80 |
| 44 | — | — | Cl | — | — | OCH$_3$ | —C=C— | p | 122–122.5 |
| 45 | — | — | Br | — | — | OCH$_3$ | —C=C— | p | 122.5–126.5 |

TABLE 1-continued

| Compound No. | Substituents X 2 | 3 | 4 | 5 | 6 | R | A | Bonding position | Melting point (°C.) |
|---|---|---|---|---|---|---|---|---|---|
| 46 | — | — | F | — | — | OCH₃ | —C=C— | p | 111–112 |
| 47 | — | CH₃ | — | — | — | OCH₃ | —C=C— | p | 74–76 |
| 48 | — | — | CH₃ | — | — | OCH₃ | —C=C— | p | 114–115.5 |
| 49 | — | CF₃ | — | — | — | OCH₃ | —C=C— | p | 91.5–93 |
| 50 | Cl | Cl | — | — | — | OCH₃ | —C=C— | p | 102–103 |
| 51 | Cl | — | Cl | — | — | OCH₃ | —C=C— | p | 123.5–124.5 |
| 52 | Cl | — | — | Cl | — | OCH₃ | —C=C— | p | 85–90.5 |
| 53 | Cl | — | — | — | Cl | OCH₃ | —C=C— | p | 126–127 |
| 54 | — | Cl | Cl | — | — | OCH₃ | —C=C— | p | 126–128 |
| 55 | — | Cl | — | Cl | — | OCH₃ | —C=C— | p | 91–92 |
| 56 | CH₃ | — | — | CH₃ | — | OCH₃ | —C=C— | p | 98–99 |
| 57 | CH₃ | — | — | — | CH₃ | OCH₃ | —C=C— | p | 118.5–119.5 |
| 58 | CH₃ | — | Cl | — | — | OCH₃ | —C=C— | p | 112–113.5 |
| 59 | — | CH₃ | Cl | — | — | OCH₃ | —C=C— | p | 107–108 |
| 60 | Cl | — | — | — | CH₃ | OCH₃ | —C=C— | p | 115–116.5 |
| 61 | Cl | — | Cl | Cl | — | OCH₃ | —C=C— | p | 130–131 |
| 62 | CH₃ | — | CH₃ | — | CH₃ | OCH₃ | —C=C— | p | 114–116 |
| 63 | — | — | — | — | — | CH₃ | —C=C— | m | 102–104 |
| 64 | Cl | — | — | — | — | CH₃ | —C=C— | m | 132–132.5 |
| 65 | — | Cl | — | — | — | CH₃ | —C=C— | m | 126.5–127.5 |

TABLE 1-continued

| Compound No. | Substituents X 2 | 3 | 4 | 5 | 6 | R | A | Bonding position | Melting point (°C.) |
|---|---|---|---|---|---|---|---|---|---|
| 66 | — | — | Cl | — | — | CH$_3$ | —C=C— | m | 140.5–141.5 |
| 67 | — | — | Br | — | — | CH$_3$ | —C=C— | m | 134.5–135.5 |
| 68 | — | — | F | — | — | CH$_3$ | —C=C— | m | 132.5–134 |
| 69 | — | CH$_3$ | — | — | — | CH$_3$ | —C=C— | m | 128–129 |
| 70 | — | — | CH$_3$ | — | — | CH$_3$ | —C=C— | m | 145–145.5 |
| 71 | — | CF$_3$ | — | — | — | CH$_3$ | —C=C— | m | 134–135 |
| 72 | Cl | Cl | — | — | — | CH$_3$ | —C=C— | m | 142–143.5 |
| 73 | Cl | — | Cl | — | — | CH$_3$ | —C=C— | m | 136–138 |
| 74 | Cl | — | — | Cl | — | CH$_3$ | —C=C— | m | 147–148 |
| 75 | Cl | — | — | — | Cl | CH$_3$ | —C=C— | m | 95–96 |
| 76 | — | Cl | Cl | — | — | CH$_3$ | —C=C— | m | 126–127 |
| 77 | — | Cl | — | Cl | — | CH$_3$ | —C=C— | m | 117.5–119.5 |
| 78 | CH$_3$ | — | — | CH$_3$ | — | CH$_3$ | —C=C— | m | 165–166 |
| 79 | CH$_3$ | — | — | — | CH$_3$ | CH$_3$ | —C=C— | m | 88 |
| 80 | CH$_3$ | — | Cl | — | — | CH$_3$ | —C=C— | m | 116–118 |
| 81 | — | CH$_3$ | Cl | — | — | CH$_3$ | —C=C— | m | 119–120 |
| 82 | Cl | — | — | — | CH$_3$ | CH$_3$ | —C=C— | m | 98–99 |
| 83 | Cl | — | Cl | Cl | — | CH$_3$ | —C=C— | m | 173.5–174.5 |
| 84 | CH$_3$ | — | CH$_3$ | — | CH$_3$ | CH$_3$ | —C=C— | m | 111.5–113 |
| 85 | — | — | — | — | — | OCH$_3$ | —C=C— | m | 86–87 |

TABLE 1-continued

| Compound No. | Substituents X 2 | 3 | 4 | 5 | 6 | R | A | Bonding position | Melting point (°C.) |
|---|---|---|---|---|---|---|---|---|---|
| 86 | Cl | — | — | — | — | OCH₃ | —C=C— | m | 72-74 |
| 87 | — | Cl | — | — | — | OCH₃ | —C=C— | m | 61-63 |
| 88 | — | — | Cl | — | — | OCH₃ | —C=C— | m | 113.5-115 |
| 89 | — | — | Br | — | — | OCH₃ | —C=C— | m | 99-100 |
| 90 | F | — | — | — | — | OCH₃ | —C=C— | m | 0.1 |
| 91 | — | F | — | — | — | OCH₃ | —C=C— | m | oil |
| 92 | — | — | F | — | — | OCH₃ | —C=C— | m | 101-102.5 |
| 93 | CH₃ | — | — | — | — | OCH₃ | —C=C— | m | oil |
| 94 | — | CH₃ | — | — | — | OCH₃ | —C=C— | m | oil |
| 95 | — | — | CH₃ | — | — | OCH₃ | —C=C— | m | 131-132 |
| 96 | — | CF₃ | — | — | — | OCH₃ | —C=C— | m | oil |
| 97 | Cl | Cl | — | — | — | OCH₃ | —C=C— | m | oil |
| 98 | Cl | — | Cl | — | — | OCH₃ | —C=C— | m | 91-92 |
| 99 | Cl | — | — | Cl | — | OCH₃ | —C=C— | m | oil |
| 100 | Cl | — | — | — | Cl | OCH₃ | —C=C— | m | oil |
| 101 | — | Cl | Cl | — | — | OCH₃ | —C=C— | m | oil |
| 102 | — | Cl | — | Cl | — | OCH₃ | —C=C— | m | oil |
| 103 | CH₃ | CH₃ | — | — | — | OCH₃ | —C=C— | m | oil |
| 104 | CH₃ | — | CH₃ | — | — | OCH₃ | —C=C— | m | 84.5-85 |
| 105 | CH₃ | — | — | CH₃ | — | OCH₃ | —C=C— | m | oil |

TABLE 1-continued

| Compound No. | Substituents X 2 | 3 | 4 | 5 | 6 | R | A | Bonding position | Melting point (°C.) |
|---|---|---|---|---|---|---|---|---|---|
| 106 | CH₃ | — | — | — | CH₃ | OCH₃ | —C=C— | m | oil |
| 107 | — | CH₃ | CH₃ | — | — | OCH₃ | —C=C— | m | 109.5–110 |
| 108 | — | CH₃ | — | CH₃ | — | OCH₃ | —C=C— | m | oil |
| 109 | CH₃ | — | Cl | — | — | OCH₃ | —C=C— | m | 81–82 |
| 110 | — | CH₃ | Cl | — | — | OCH₃ | —C=C— | m | 88–90 |
| 111 | Cl | — | — | — | CH₃ | OCH₃ | —C=C— | m | oil |
| 112 | Cl | — | Cl | Cl | — | OCH₃ | —C=C— | m | oil |
| 113 | Cl | — | Cl | — | Cl | OCH₃ | —C=C— | m | oil |
| 114 | CH₃ | — | CH₃ | — | CH₃ | OCH₃ | —C=C— | m | oil |
| 115 | — | — | — | — | — | CH₃ | —C≡C— | p | 91–92 |
| 116 | Cl | — | — | — | — | CH₃ | —C≡C— | p | 102.5–103.5 |
| 117 | — | Cl | — | — | — | CH₃ | —C≡C— | p | 106.5–107.5 |
| 118 | — | — | Cl | — | — | CH₃ | —C≡C— | p | 118 |
| 119 | — | — | Br | — | — | CH₃ | —C≡C— | p | 115–115.5 |
| 120 | F | — | — | — | — | CH₃ | —C≡C— | p | 110–110.5 |
| 121 | — | F | — | — | — | CH₃ | —C≡C— | p | 95–96 |
| 122 | — | — | F | — | — | CH₃ | —C≡C— | p | 96–97 |
| 123 | CH₃ | — | — | — | — | CH₃ | —C≡C— | p | 86 |
| 124 | — | CH₃ | — | — | — | CH₃ | —C≡C— | p | 94.5–95 |
| 125 | — | — | CH₃ | — | — | CH₃ | —C≡C— | p | 106–197 |
| 126 | — | — | Et | — | — | CH₃ | —C≡C— | p | 81.5–82 |
| 127 | Cl | Cl | — | — | — | CH₃ | —C≡C— | p | 124.5–125 |
| 128 | Cl | — | Cl | — | — | CH₃ | —C≡C— | p | 95.5–96 |
| 129 | Cl | — | — | Cl | — | CH₃ | —C≡C— | p | 92.5–93.5 |
| 130 | Cl | — | — | — | Cl | CH₃ | —C≡C— | p | 114.5–115.5 |
| 131 | — | Cl | Cl | — | — | CH₃ | —C≡C— | p | 113–114 |
| 132 | — | Cl | — | Cl | — | CH₃ | —C≡C— | p | 118.5–119.5 |
| 133 | CH₃ | CH₃ | — | — | — | CH₃ | —C≡C— | p | 145.5–146 |
| 134 | CH₃ | — | CH₃ | — | — | CH₃ | —C≡C— | p | 108–109 |
| 135 | CH₃ | — | — | CH₃ | — | CH₃ | —C≡C— | p | 124.5–125.5 |
| 136 | CH₃ | — | — | — | CH₃ | CH₃ | —C≡C— | p | 125 |
| 137 | — | CH₃ | CH₃ | — | — | CH₃ | —C≡C— | p | 137.5–138 |
| 138 | — | CH₃ | — | CH₃ | — | CH₃ | —C≡C— | p | 145–146 |
| 139 | CH₃ | — | Cl | — | — | CH₃ | —C≡C— | p | 120–121 |
| 140 | — | CH₃ | Cl | — | — | CH₃ | —C≡C— | p | 113.5–115 |
| 141 | Cl | — | — | — | CH₃ | CH₃ | —C≡C— | p | 107.5–108 |
| 142 | Cl | — | Cl | Cl | — | CH₃ | —C≡C— | p | 140–141 |
| 143 | — | CH₃ | Cl | CH₃ | — | CH₃ | —C≡C— | p | 139–140 |
| 144 | — | — | — | — | — | OCH₃ | —C≡C— | p | 86.5–87.5 |
| 145 | Cl | — | — | — | — | OCH₃ | —C≡C— | p | 66.5–67.5 |
| 146 | — | Cl | — | — | — | OCH₃ | —C≡C— | p | oil |
| 147 | — | — | Cl | — | — | OCH₃ | —C≡C— | p | 97.5–98 |
| 148 | — | F | — | — | — | OCH₃ | —C≡C— | p | 68–68.5 |
| 149 | — | — | F | — | — | OCH₃ | —C≡C— | p | 76–76.5 |
| 150 | CH₃ | — | — | — | — | ICG₃ | —C≡C— | p | 70 |
| 151 | — | CH₃ | — | — | — | OCH₃ | —C≡C— | p | oil |
| 152 | — | — | CH₃ | — | — | OCH₃ | —C≡C— | p | 77.5–78 |
| 153 | Cl | Cl | — | — | — | OCH₃ | —C≡C— | p | 128.5–130.5 |
| 154 | Cl | — | Cl | — | — | OCH₃ | —C≡C— | p | 87–88 |
| 155 | Cl | — | — | Cl | — | OCH₃ | —C≡C— | p | 57–58 |
| 156 | Cl | — | — | — | Cl | OCH₃ | —C≡C— | p | 116–117 |
| 157 | — | Cl | Cl | — | — | OCH₃ | —C≡C— | p | 86–87 |

TABLE 1-continued

| Compound No. | Substituents X 2 | 3 | 4 | 5 | 6 | R | A | Bonding position | Melting point (°C.) |
|---|---|---|---|---|---|---|---|---|---|
| 158 | — | Cl | — | Cl | — | OCH₃ | —C≡C— | p | 75.5–76 |
| 159 | CH₃ | CH₃ | — | — | — | OCH₃ | —C≡C— | p | 93.5–94.5 |
| 160 | CH₃ | — | CH₃ | — | — | OCH₃ | —C≡C— | p | 78.5–79.5 |
| 161 | CH₃ | — | — | CH₃ | — | OCH₃ | —C≡C— | p | 98–98.5 |
| 162 | CH₃ | — | — | — | CH₃ | OCH₃ | —C≡C— | p | 93–93.5 |
| 163 | — | CH₃ | CH₃ | — | — | OCH₃ | —C≡C— | p | 101–102 |
| 164 | — | CH₃ | — | CH₃ | — | OCH₃ | —C≡C— | p | 84 |
| 165 | CH₃ | — | Cl | — | — | OCH₃ | —C≡C— | p | 91.5–92 |
| 166 | — | CH₃ | Cl | — | — | OCH₃ | —C≡C— | p | 79.5–80 |
| 167 | Cl | — | — | — | CH₃ | OCH₃ | —C≡C— | p | 99–100 |
| 168 | — | — | — | — | — | OCH₃ | —C≡C— | m | 123–124 |
| 169 | — | Cl | — | — | — | CH₃ | —C≡C— | m | 102.5–103.5 |
| 170 | — | — | Cl | — | — | CH₃ | —C≡C— | m | 151.5–152.5 |
| 171 | — | — | F | — | — | CH₃ | —C≡C— | m | 149.5–150 |
| 172 | — | — | CH₃ | — | — | CH₃ | —C≡C— | m | 119.5–120.5 |
| 173 | i-pr | — | — | — | — | CH₃ | —C≡C— | m | 88 |
| 174 | Cl | — | Cl | — | — | CH₃ | —C≡C— | m | 121.5–122.5 |
| 175 | Cl | — | — | Cl | — | CH₃ | —C≡C— | m | 94.5–95.5 |
| 176 | Cl | — | — | — | Cl | CH₃ | —C≡C— | m | 124.5–125.5 |
| 177 | — | Cl | Cl | — | — | CH₃ | —C≡C— | m | 129–130 |
| 178 | — | Cl | — | Cl | — | CH₃ | —C≡C— | m | 114.5–115.5 |
| 179 | CH₃ | — | — | — | CH₃ | CH₃ | —C≡C— | m | 128–129 |
| 180 | — | CH₃ | CH₃ | — | — | CH₃ | —C≡C— | m | 120.5–122.5 |
| 181 | CH₃ | — | Cl | — | — | CH₃ | —C≡C— | m | 119–120.5 |
| 182 | — | CH₃ | Cl | — | — | CH₃ | —C≡C— | m | 98–99 |
| 183 | Cl | — | — | — | CH₃ | CH₃ | —C≡C— | m | 122.5–123.5 |
| 184 | Cl | — | Cl | Cl | — | CH₃ | —C≡C— | m | 134–135 |
| 185 | — | — | — | — | — | OCH₃ | —C≡C— | m | 74.5–75.5 |
| 186 | — | Cl | — | — | — | OCH₃ | —C≡C— | m | oil |
| 187 | — | — | Cl | — | — | OCH₃ | —C≡C— | m | 90–91 |
| 188 | — | F | — | — | — | OCH₃ | —C≡C— | m | 45–46 |
| 189 | — | CH₃ | — | — | — | OCH₃ | —C≡C— | m | oil |
| 190 | i-pr | — | — | — | — | OCH₃ | —C≡C— | m | 71–73 |
| 191 | — | CF₃ | — | — | — | OCH₃ | —C≡C— | m | 57.5–58.5 |
| 192 | Cl | Cl | — | — | — | OCH₃ | —C≡C— | m | 96–97 |
| 193 | Cl | — | Cl | — | — | OCH₃ | —C≡C— | m | 100–101 |
| 194 | Cl | — | — | Cl | — | OCH₃ | —C≡C— | m | 75–76 |
| 195 | Cl | — | — | — | Cl | OCH₃ | —C≡C— | m | 69–70 |
| 196 | — | Cl | Cl | — | — | OCH₃ | —C≡C— | m | 72–73 |
| 197 | — | Cl | — | Cl | — | OCH₃ | —C≡C— | m | 87–88 |
| 198 | CH₃ | — | CH₃ | — | — | OCH₃ | —C≡C— | m | 74.5–75 |
| 199 | CH₃ | — | — | CH₃ | — | OCH₃ | —C≡C— | m | 84.5–85.5 |
| 200 | CH₃ | — | — | — | CH₃ | OCH₃ | —C≡C— | m | oil |
| 201 | — | CH₃ | CH₃ | — | — | OCH₃ | —C≡C— | m | 93.5–94.5 |
| 202 | — | CH₃ | — | CH₃ | — | OCH₃ | —C≡C— | m | 96–97 |
| 203 | CH₃ | — | Cl | — | — | OCH₃ | —C≡C— | m | 95.5–96.5 |
| 204 | — | CH₃ | Cl | — | — | OCH₃ | —C≡C— | m | 78–79 |
| 205 | Cl | — | — | — | CH₃ | OCH₃ | —C≡C— | m | 76–78 |
| 206 | Cl | — | Cl | Cl | — | OCH₃ | —C≡C— | m | 79.5–80.5 |

TABLE 2

| Compound No. | NMR spectra (δ)(CDCl₃) |
|---|---|
| 90 | 3.15(3H,s), 3.73(3H,s), 4.55(4H,m), 6.03(2H,m), 6.48–7.30(8H), 7.67(1H,bs) |
| 91 | 3.15(3H,s), 3.72(3H,s), 4.54(4H,m), 6.00(2H,m), 6.47–7.30(8H), 7.68(1H,bs) |
| 93 | 2.23(3H,s), 3.16(3H,s), 3.73(3H,s), 4.55(4H,m), 6.05(2H,m), 6.52–7.30(8H), 7.69(1H,bs) |
| 94 | 2.32(3H,s), 3.16(3H,s), 3.74(3H,s), 4.55(4H,m), 6.05(2H,m), 6.50–7.30(8H), 7.70(1H,bs) |
| 96 | 3.16(3H,s), 3.72(3H,s), 4.54(4H,m), 6.03(2H,m), 6.50–7.37(8H), 7.65(1H,bs) |
| 97 | 3.15(3H,s), 3.71(3H,s), 4.56(4H,m), 6.06(2H,m), 6.45–7.30(7H), 7.66(1H,bs) |
| 99 | 3.15(3H,s), 3.72(3H,s), 4.55(4H,m), 6.02(2H,m), 6.49–7.32(7H), 7.70(1H,bs) |
| 100 | 3.16(3H,s), 3.73(3H,s), 4.55(4H,m), 6.07(2H,m), 6.52–7.35(7H), 7.67(1H,bs) |
| 101 | 3.15(3H,s), 3.72(3H,s), 4.50(4H,m), 5.98(2H,m), 6.48–7.35(7H), 7.69(1H,bs) |
| 102 | 3.15(3H,s), 3.73(3H,s), 4.51(4H,m), 6.00(2H,m), 6.50–7.30(7H), 7.68(1H,bs) |
| 103 | 2.15(3H,s), 2.25(3H,s), 3.16(3H,s), 3.72(3H,s), 4.54(4H,m), 6.06(2H,m), 6.50–7.30(7H), 7.67(1H,m) |
| 105 | 2.19(3H,s), 2.29(3H,s), 3.15(3H,s), 3.71(3H,s), 4.51(4H,m), 6.03(2H,m), 6.49–7.30(7H), 7.67(1H,m) |
| 106 | 2.24(6H,s), 3.14(3H,s), 3.71(3H,s), 4.30(2H,m), 4.53(2H,m), 6.05(2H,m), 6.48–7.31(7H), 7.65(1H,m) |
| 108 | 2.26(6H,s), 3.15(3H,s), 3.72(3H,s), 4.51(4H,m), 6.03(2H,m), 6.47–7.31(7H), 7.70(1H,bs) |
| 111 | 2.27(3H,s), 3.15(3H,s), 3.73(3H,s), 4.51(4H,m), 6.10(2H,m), 6.50–7.31(7H), 7.67(1H,bs) |
| 112 | 3.14(3H,s), 3.71(3H,s), 4.52(4H,m), 5.98(2H,m), 6.49–7.40(6H), 7.67(1H,bs) |
| 113 | 3.16(3H,s), 3.72(3H,s), 4.55(4H,m), 6.07(2H,m), 6.50–7.30(6H), 7.69(1H,bs) |
| 114 | 2.20(9H,s), 3.14(3H,s), 3.71(3H,s), 4.27(2H,m), 4.54(2H,m), 6.06(2H,m), |

TABLE 2-continued

| Compound No. | NMR spectra (δ)(CDCl₃) |
|---|---|
| | 6.52–7.30(6H), 7.64(1H,bs) |

In practice, one or more compounds of this invention are usually applied to the field at a rate between 50 and 2000 g per 10 ares, preferably 100 and 1000 g per 10 ares, although the application rate may vary depending upon the conditions such as particular species and infestation level of weeds, particular herbicidal compound to be used.

The compounds of this invention can be applied in various ways to achieve herbicidal action. Although they can be applied per se, they are preferably applied by formulating them into a suitable form.

They can be formulated by a conventional way into various forms, such as solution, dispersion, emulsifiable concentrate, with a suitable liquid medium and forms such as wettable powder, granule, dust and tablet with a suitable solid carrier. Upon formulation, necessary additives must be used, such as emulsifier, dispersant, spreader, penetrant, stabilizer and the like.

The active compound of this invention may be used with both solvent and non-solvent liquid mediums. Suitable liquid mediums include for example, alcohols such as methanol, ethanol, ethyleneglycol and the like; ketones such as acetone, methyl ethyl ketone and the like; ethers such as dioxane, tetrahydrofuran, cellosolves and the like; hydrocarbons such as benzene, toluene, xylene, hexane, kerosine, naphtha, methylnaphthalene and the like; esters such as ethyl acetate, butyl acetate, and the like; organic bases such as pyridine, picoline and the like; and other organic solvents such as dimethylformamide, acetonitrile and the like.

The solid carrier which is useful in this invention includes diluents and fillers, for example, mineral powder such as kaoline, bentonite, clay, acid clay, diatom earth, mica powder, alumina and the like; and vegetable powder such as soy powder, flour, wood powder, active charcoal and the like; and mixtures thereof. For the emulsifier, dispersant, penetrant or spreader, any type of surfactant can be used such as anionic, cationic, nonionic or amphoteric surfactant.

Caseine, gelatin, starch, sodium alginate may be used as an optional adjuvant for the formulation.

Although the compound of this invention can be used in any suitable proportion in the formulation, the content usually ranges from 5 to 90% by weight based on the total formulation.

The herbicidal composition of this invention may also be combined with other types of active compound, fungicidal ingredient, insecticidal ingredient, plant-growth regulator, fertilizer depending upon the particular application.

The invention is further illustrated by the following Examples and Experiments, but the described particular active compound, carriers, adjuvants and proportions are by no means intended to limit the scope of this invention.

The proportions in terms of part of percent are based on weight, unless definition is given otherwise.

Example 1: Preparation of Wettable Powder

| Compound No. 32 | 50 parts |
|---|---|

-continued

| Sodium lignin sulfonate | 1 part |
|---|---|
| Polyoxyethylene alkylaryl ether | 4 parts |
| Clay | 45 parts |

These components were mixed thoroughly, and pulverized to form a wettable powder herbicide.

Example 2: Preparation of Emulsifiable Concentrate

| Compound No. 102 | 20 parts |
|---|---|
| Alkylbenzene sulfonate | 3 parts |
| Polyoxyethylene alkylaryl ether | 10 parts |
| Xylene | 67 parts |

The components were mixed thoroughly to form homogeneous emulsifiable concentrate.

Example 3: Preparation of Granules

| Compound No. 203 | 6 parts |
|---|---|
| Bentonite | 30 parts |
| Sodium alkylsulfate | 1.5 parts |
| Clay | 62.5 parts |

The components were mixed and intimately kneaded, and processed by a conventional way to form granules.

Example 4: Preparation of Dust

| Compound No. 139 | 7 parts |
|---|---|
| Clay | 93 parts |

The components were thoroughly blended to form a dust herbicide.

EXPERIMENT 1

Polyethylene post having a surface area of 1/5000 areas were filled with paddy field soil (clayish loam). The pots were seeded with barnyard grass (*Echinochloa Crusgalli P. Beauv var. orizicola Ohwi*), Cyperaceous weed (*Cyperus difformis L.*) and some broadleaf weeds in a 2-cm depth soil layer. At the same time, 2-leaf stage rice plant seedlings were transplanted in the pots at a depth of 2 cm with two seedlings together per spot. Then, the pots were submerged in water 3 cm below the water level.

When starting the germination of the weeds, the herbicidal composition formulated in Example 1 was weighed in a predetermined amount and diluted with 10 ml of water per pot and added dropwise to the water in each pot. The pots were placed in a greedhouse to allow the rice plant and the weeds to grow. Three weeks after the treatment, the levels of herbicidal activity and phytotoxicity were observed on each pot.

The results are shown in Table 3 below.

In Table 3 the level of phytotoxicity against phytotoxic level of rice plant and herbicidal activity against weeds were rated on the following scale of from 1–5.

| Scale | Pytotoxicity | Herbicidal Effects |
|---|---|---|
| 5 | death | 100% controlled (amount of weeds 0%) |
| 4 | severe injury | 80% controlled (amount of weeds 20%) |
| 3 | moderately severe | 60% controlled (amount of weeds 40%) |

| Scale | Pytotoxicity | Herbicidal Effects |
|---|---|---|
| 2 | injury moderate injury | 40% controlled (amount of weeds 60%) |
| 1 | slight injury | 20% controlled (amount of weeds 80%) |
| 0 | no injury | 0% controlled (amount of weeds 100%) |

TABLE 3

| Compound No. | Application Rate (g/10a) | Phytotoxicity to Rice | Herbicidal Effect Barnyard grass | Cyperaceous weed | Broadleak weed |
|---|---|---|---|---|---|
| 1 | 250 | 1 | 5 | 5 | 5 |
|   | 500 | 3 | 5 | 5 | 5 |
|   | 1000 | 4 | 5 | 5 | 5 |
| 2 | 250 | 1 | 5 | 5 | 5 |
|   | 500 | 2 | 5 | 5 | 5 |
|   | 1000 | 4 | 5 | 5 | 5 |
| 3 | 250 | 0 | 4 | 5 | 5 |
|   | 500 | 1 | 4.5 | 5 | 5 |
|   | 1000 | 2 | 5 | 5 | 5 |
| 4 | 250 | 0 | 4 | 5 | 5 |
|   | 500 | 0 | 4.5 | 5 | 5 |
|   | 1000 | 0 | 5 | 5 | 5 |
| 5 | 250 | 0 | 2 | 2 | 4 |
|   | 500 | 0 | 3 | 3 | 4 |
|   | 1000 | 0 | 3 | 3 | 4.5 |
| 6 | 250 | 0 | 5 | 1 | 5 |
|   | 500 | 0 | 5 | 2 | 5 |
|   | 1000 | 1 | 5 | 4 | 5 |
| 7 | 250 | 1 | 3 | 5 | 5 |
|   | 500 | 3 | 4 | 5 | 5 |
|   | 1000 | 4 | 5 | 5 | 5 |
| 8 | 250 | 1 | 4.5 | 5 | 5 |
|   | 500 | 3 | 5 | 5 | 5 |
|   | 1000 | 4 | 5 | 5 | 5 |
| 9 | 250 | 1 | 4 | 5 | 5 |
|   | 500 | 2 | 5 | 5 | 5 |
|   | 1000 | 3 | 5 | 5 | 5 |
| 10 | 250 | 1 | 5 | 5 | 5 |
|   | 500 | 2 | 5 | 5 | 5 |
|   | 1000 | 3 | 5 | 5 | 5 |
| 11 | 250 | 0 | 3 | 3 | 4 |
|   | 500 | 0 | 4 | 5 | 5 |
|   | 1000 | 0 | 4 | 5 | 5 |
| 19 | 250 | 0 | 5 | 1 | 5 |
|   | 500 | 0 | 5 | 2 | 5 |
|   | 1000 | 0 | 5 | 4.5 | 5 |
| 20 | 250 | 0 | 5 | 4 | 5 |
|   | 500 | 0 | 5 | 5 | 5 |
|   | 1000 | 0 | 5 | 5 | 5 |
| 21 | 250 | 0 | 3 | 5 | 5 |
|   | 500 | 0 | 4 | 5 | 5 |
|   | 1000 | 0 | 4.5 | 5 | 5 |
| 22 | 250 | 0 | 5 | 4 | 5 |
|   | 500 | 0 | 5 | 4.5 | 5 |
|   | 1000 | 0 | 5 | 5 | 5 |
| 23 | 250 | 0 | 5 | 4 | 5 |
|   | 500 | 0 | 5 | 4 | 5 |
|   | 1000 | 0 | 5 | 4.5 | 5 |
| 24 | 250 | 0 | 3 | 4 | 5 |
|   | 500 | 0 | 4 | 4 | 5 |
|   | 1000 | 0 | 4 | 4.5 | 5 |
| 25 | 250 | 0 | 4 | 3 | 5 |
|   | 500 | 0 | 4.5 | 4 | 5 |
|   | 1000 | 0 | 5 | 4 | 5 |
| 26 | 250 | 0 | 2 | 2 | 5 |
|   | 500 | 0 | 3 | 2 | 5 |
|   | 1000 | 0 | 3 | 4.5 | 5 |
| 27 | 250 | 0 | 3 | 3 | 5 |
|   | 500 | 0 | 5 | 4.5 | 5 |
|   | 1000 | 0 | 5 | 5 | 5 |
| 28 | 250 | 0 | 5 | 4.5 | 5 |
|   | 500 | 0 | 5 | 5 | 5 |
|   | 100 | 0 | 5 | 5 | 5 |
| 29 | 250 | 0 | 4 | 4.5 | 5 |
|   | 500 | 0 | 5 | 5 | 5 |
|   | 1000 | 0 | 5 | 5 | 5 |
|   | 250 | 0 | 4 | 4 | 5 |
| 30 | 500 | 0 | 4.5 | 4.5 | 5 |
|   | 1000 | 0 | 4.5 | 5 | 5 |
| 31 | 250 | 0 | 4.5 | 4 | 5 |
|   | 500 | 0 | 5 | 4.5 | 5 |
|   | 1000 | 0 | 5 | 5 | 5 |
| 32 | 250 | 0 | 5 | 5 | 5 |
|   | 500 | 0 | 5 | 5 | 5 |
|   | 1000 | 0 | 5 | 5 | 5 |
| 33 | 250 | 0 | 5 | 4 | 5 |
|   | 500 | 0 | 5 | 4.5 | 5 |
|   | 1000 | 0 | 5 | 5 | 5 |
| 34 | 250 | 0 | 5 | 2 | 5 |
|   | 500 | 0 | 5 | 2 | 5 |
|   | 1000 | 0 | 5 | 3 | 5 |
| 36 | 250 | 0 | 5 | 3 | 5 |
|   | 500 | 0 | 5 | 4 | 5 |
|   | 1000 | 0 | 5 | 4.5 | 5 |
| 37 | 250 | 0 | 2 | 1 | 5 |
|   | 500 | 0 | 3 | 3 | 5 |
|   | 1000 | 0 | 4 | 4 | 5 |
| 38 | 250 | 0 | 4 | 4.5 | 5 |
|   | 500 | 0 | 5 | 5 | 5 |
|   | 1000 | 0 | 5 | 5 | 5 |
| 41 | 250 | 0 | 4.5 | 5 | 5 |
|   | 500 | 1 | 5 | 5 | 5 |
|   | 1000 | 1.5 | 5 | 5 | 5 |
| 42 | 250 | 0 | 2 | 1 | 5 |
|   | 500 | 0 | 3 | 2 | 5 |
|   | 1000 | 0 | 4.5 | 4 | 5 |
| 43 | 250 | 0 | 4.5 | 5 | 5 |
|   | 500 | 0 | 5 | 5 | 5 |
|   | 1000 | 0 | 5 | 5 | 5 |
| 44 | 250 | 0 | 4 | 1 | 4 |
|   | 500 | 0 | 4.5 | 2 | 4.5 |
|   | 1000 | 0 | 5 | 3 | 5 |
| 46 | 250 | 0 | 4 | 1 | 4 |
|   | 500 | 0 | 4.5 | 1 | 4.5 |
|   | 1000 | 0 | 5 | 2 | 5 |
| 47 | 250 | 0 | 4.5 | 1 | 5 |
|   | 500 | 0 | 5 | 2 | 5 |
|   | 1000 | 0 | 5 | 4 | 5 |
| 48 | 250 | 0 | 3 | 1 | 5 |
|   | 500 | 0 | 4 | 2 | 5 |
|   | 1000 | 0 | 4.5 | 3 | 5 |
| 51 | 250 | 0 | 1 | 1 | 5 |
|   | 500 | 0 | 2 | 2 | 5 |
|   | 1000 | 0 | 3 | 2 | 5 |
| 54 | 250 | 0 | 4 | 1 | 4 |
|   | 500 | 0 | 4.5 | 2 | 4 |
|   | 1000 | 0 | 5 | 3 | 5 |
| 58 | 250 | 0 | 2 | 1 | 4 |
|   | 500 | 0 | 2 | 1 | 4.5 |
|   | 1000 | 0 | 3 | 2 | 5 |
| 63 | 250 | 0 | 4 | 5 | 5 |
|   | 500 | 0 | 4.5 | 5 | 5 |
|   | 1000 | 0 | 5 | 5 | 5 |
| 64 | 250 | 0 | 4 | 1 | 4 |
|   | 500 | 0 | 4.5 | 2 | 4.5 |
|   | 1000 | 0 | 5 | 3 | 5 |
| 65 | 250 | 0 | 4 | 1 | 5 |
|   | 500 | 0 | 4.5 | 2 | 5 |
|   | 1000 | 0 | 5 | 4 | 5 |
| 66 | 250 | 0 | 4 | 1 | 4.5 |
|   | 500 | 0 | 4.5 | 2 | 5 |
|   | 1000 | 0 | 5 | 2 | 5 |
| 67 | 250 | 0 | 4 | 4.5 | 5 |
|   | 500 | 0 | 4.5 | 5 | 5 |
|   | 1000 | 0 | 5 | 5 | 5 |
| 68 | 250 | 0 | 5 | 2 | 4.5 |
|   | 500 | 0 | 5 | 4 | 5 |
|   | 1000 | 0 | 5 | 5 | 5 |
| 69 | 250 | 0 | 5 | 2 | 5 |
|   | 500 | 0 | 5 | 2 | 5 |
|   | 1000 | 0 | 5 | 3 | 5 |
| 70 | 250 | 0 | 4 | 1 | 3 |
|   | 500 | 0 | 5 | 2 | 3 |
|   | 1000 | 0 | 5 | 3 | 4 |

TABLE 3-continued

| Compound No. | Application Rate (g/10a) | Phytotoxicity to Rice | Herbicidal Effect | | |
|---|---|---|---|---|---|
| | | | Barnyard grass | Cyperaceous weed | Broadleak weed |
| | 250 | 0 | 3 | 4.5 | 5 |
| 71 | 400 | 0 | 4 | 5 | 5 |
| | 1000 | 0 | 4.5 | 5 | 5 |
| | 250 | 0 | 3 | 4 | 5 |
| 72 | 500 | 0 | 4 | 4.5 | 5 |
| | 1000 | 0 | 4.5 | 5 | 5 |
| | 250 | 0 | 5 | 1 | 4 |
| 73 | 500 | 0 | 5 | 2 | 4.5 |
| | 1000 | 0 | 5 | 3 | 5 |
| | 250 | 0 | 4 | 1 | 5 |
| 74 | 500 | 0 | 4.5 | 2 | 5 |
| | 1000 | 1 | 5 | 3 | 5 |
| | 250 | 0 | 4 | 5 | 5 |
| 75 | 500 | 0 | 4.5 | 5 | 5 |
| | 1000 | 0 | 5 | 5 | 5 |
| | 250 | 0 | 3 | 3 | 4.5 |
| 76 | 500 | 0 | 4 | 4.5 | 5 |
| | 1000 | 0 | 4.5 | 5 | 5 |
| | 250 | 0 | 4 | 4.5 | 5 |
| 77 | 500 | 0 | 4 | 5 | 5 |
| | 1000 | 0 | 5 | 5 | 5 |
| | 250 | 0 | 2 | 4 | 5 |
| 78 | 500 | 0 | 3 | 5 | 5 |
| | 1000 | 0 | 4 | 5 | 5 |
| | 250 | 0 | 5 | 1 | 4 |
| 80 | 500 | 0 | 5 | 2 | 4.5 |
| | 1000 | 0 | 5 | 2 | 5 |
| | 250 | 0 | 3 | 4.5 | 5 |
| 81 | 500 | 0 | 4 | 5 | 5 |
| | 1000 | 0 | 4 | 5 | 5 |
| | 250 | 0 | 4 | 5 | 5 |
| 82 | 500 | 0 | 4.5 | 5 | 5 |
| | 1000 | 0 | 5 | 5 | 5 |
| | 250 | 0 | 5 | 5 | 5 |
| 85 | 500 | 1 | 5 | 5 | 5 |
| | 1000 | 1.5 | 5 | 5 | 5 |
| | 250 | 0 | 5 | 4 | 5 |
| 86 | 500 | 0 | 5 | 5 | 5 |
| | 1000 | 0 | 5 | 5 | 5 |
| | 250 | 0 | 5 | 4.5 | 5 |
| 87 | 500 | 0 | 5 | 5 | 5 |
| | 1000 | 0 | 5 | 5 | 5 |
| | 250 | 0 | 4 | 4 | 5 |
| 88 | 500 | 0 | 5 | 4.5 | 5 |
| | 1000 | 0 | 5 | 5 | 5 |
| | 250 | 0 | 4 | 4 | 5 |
| 89 | 500 | 0 | 4.5 | 5 | 5 |
| | 1000 | 0 | 5 | 5 | 5 |
| | 250 | 0 | 5 | 5 | 5 |
| 90 | 500 | 0 | 5 | 5 | 5 |
| | 1000 | 0 | 5 | 5 | 5 |
| | 250 | 0 | 5 | 5 | 5 |
| 91 | 500 | 0 | 5 | 5 | 5 |
| | 1000 | 0 | 5 | 5 | 5 |
| | 250 | 0 | 4.5 | 3 | 5 |
| 92 | 500 | 0 | 5 | 5 | 5 |
| | 1000 | 0 | 5 | 5 | 5 |
| | 250 | 0 | 4.5 | 5 | 5 |
| 93 | 500 | 0 | 5 | 5 | 5 |
| | 1000 | 0 | 5 | 5 | 5 |
| | 250 | 0 | 5 | 4 | 5 |
| 94 | 500 | 0 | 5 | 4.5 | 5 |
| | 1000 | 0 | 5 | 5 | 5 |
| | 250 | 0 | 5 | 5 | 5 |
| 96 | 500 | 0 | 5 | 5 | 5 |
| | 1000 | 0 | 5 | 5 | 5 |
| | 250 | 0 | 4.5 | 5 | 5 |
| 97 | 500 | 0 | 5 | 5 | 5 |
| | 1000 | 0 | 5 | 5 | 5 |
| | 250 | 0 | 5 | 5 | 5 |
| 98 | 500 | 0 | 5 | 5 | 5 |
| | 1000 | 0 | 5 | 5 | 5 |
| | 250 | 0 | 5 | 5 | 5 |
| 99 | 500 | 0 | 5 | 5 | 5 |
| | 1000 | 0 | 5 | 5 | 5 |
| | 250 | 0 | 4.5 | 5 | 5 |
| 100 | 500 | 0 | 5 | 5 | 5 |
| | 1000 | 0 | 5 | 5 | 5 |
| | 250 | 0 | 4 | 1 | 5 |
| 101 | 500 | 0 | 4.5 | 2 | 5 |
| | 1000 | 0 | 5 | 3 | 5 |
| | 250 | 0 | 5 | 5 | 5 |
| 102 | 500 | 0 | 5 | 5 | 5 |
| | 1000 | 0 | 5 | 5 | 5 |
| | 250 | 0 | 4 | 5 | 5 |
| 103 | 500 | 0 | 5 | 5 | 5 |
| | 1000 | 0 | 5 | 5 | 5 |
| | 250 | 0 | 4.5 | 5 | 5 |
| 105 | 500 | 0 | 5 | 5 | 5 |
| | 1000 | 0 | 5 | 5 | 5 |
| | 250 | 0 | 5 | 5 | 5 |
| 106 | 500 | 0 | 5 | 5 | 5 |
| | 1000 | 0 | 5 | 5 | 5 |
| | 250 | 0 | 3 | 4.5 | 5 |
| 107 | 500 | 0 | 4 | 5 | 5 |
| | 1000 | 0 | 5 | 5 | 5 |
| | 250 | 0 | 5 | 5 | 5 |
| 108 | 500 | 0 | 5 | 5 | 5 |
| | 1000 | 0 | 5 | 5 | 5 |
| | 250 | 0 | 5 | 4 | 5 |
| 109 | 500 | 0 | 5 | 4.5 | 5 |
| | 1000 | 0 | 5 | 5 | 5 |
| | 250 | 0 | 4 | 4.5 | 5 |
| 110 | 500 | 0 | 4 | 5 | 5 |
| | 1000 | 0 | 5 | 5 | 5 |
| | 250 | 0 | 5 | 5 | 5 |
| 111 | 500 | 0 | 5 | 5 | 5 |
| | 1000 | 0 | 5 | 5 | 5 |
| | 250 | 0 | 4 | 5 | 5 |
| 112 | 500 | 0 | 4.5 | 5 | 5 |
| | 1000 | 0 | 5 | 5 | 5 |
| | 250 | 0 | 5 | 5 | 5 |
| 113 | 500 | 0 | 5 | 5 | 5 |
| | 1000 | 0 | 5 | 5 | 5 |
| | 250 | 0 | 5 | 3 | 5 |
| 114 | 500 | 0 | 5 | 5 | 5 |
| | 1000 | 0 | 5 | 5 | 5 |
| | 250 | 0 | 5 | 5 | 5 |
| 115 | 500 | 0 | 5 | 5 | 5 |
| | 1000 | 1.5 | 5 | 5 | 5 |
| | 250 | 0 | 5 | 4.5 | 5 |
| 116 | 500 | 0 | 5 | 5 | 5 |
| | 1000 | 0 | 5 | 5 | 5 |
| | 250 | 0 | 5 | 5 | 4.5 |
| 117 | 500 | 0 | 5 | 5 | 4.5 |
| | 1000 | 0 | 5 | 5 | 5 |
| | 250 | 0 | 5 | 4.5 | 5 |
| 118 | 500 | 0 | 5 | 5 | 5 |
| | 1000 | 0 | 5 | 5 | 5 |
| | 250 | 0 | 5 | 5 | 5 |
| 119 | 500 | 0 | 5 | 5 | 5 |
| | 1000 | 0 | 5 | 5 | 5 |
| | 250 | 0 | 4.5 | 5 | 5 |
| 120 | 500 | 1 | 5 | 5 | 5 |
| | 1000 | 1 | 5 | 5 | 5 |
| | 250 | 0 | 5 | 5 | 5 |
| 121 | 500 | 0 | 5 | 5 | 5 |
| | 1000 | 1 | 5 | 5 | 5 |
| | 250 | 1 | 5 | 4 | 5 |
| 122 | 500 | 2 | 5 | 5 | 5 |
| | 1000 | 4 | 5 | 5 | 5 |
| | 250 | 0 | 5 | 5 | 5 |
| 123 | 500 | 1 | 5 | 5 | 5 |
| | 1000 | 1 | 5 | 5 | 5 |
| | 250 | 0 | 5 | 5 | 5 |
| 124 | 500 | 1 | 5 | 5 | 5 |
| | 1000 | 1 | 5 | 5 | 5 |
| | 250 | 0 | 5 | 4 | 5 |
| 125 | 500 | 1 | 5 | 4.5 | 5 |
| | 1000 | 1 | 5 | 4.5 | 5 |
| | 250 | 0 | 5 | 5 | 5 |
| 126 | 500 | 0 | 5 | 5 | 5 |
| | 1000 | 0 | 5 | 5 | 5 |
| | 250 | 0 | 4 | 4.5 | 5 |

TABLE 3-continued

| Compound No. | Application Rate (g/10a) | Phytotoxicity to Rice | Herbicidal Effect | | |
|---|---|---|---|---|---|
| | | | Barnyard grass | Cyperaceous weed | Broadleak weed |
| 127 | 500 | 0 | 4.5 | 5 | 5 |
| | 1000 | 0 | 5 | 5 | 5 |
| 128 | 250 | 0 | 5 | 4.5 | 5 |
| | 500 | 0 | 5 | 5 | 5 |
| | 1000 | 0 | 5 | 5 | 5 |
| 129 | 250 | 0 | 5 | 5 | 5 |
| | 500 | 0 | 5 | 5 | 5 |
| | 1000 | 0 | 5 | 5 | 5 |
| 130 | 250 | 0 | 5 | 5 | 5 |
| | 500 | 0 | 5 | 5 | 5 |
| | 1000 | 0 | 5 | 5 | 5 |
| 131 | 250 | 0 | 5 | 5 | 5 |
| | 500 | 0 | 5 | 5 | 5 |
| | 1000 | 0 | 5 | 5 | 5 |
| 132 | 250 | 0 | 5 | 5 | 5 |
| | 500 | 0 | 5 | 5 | 5 |
| | 1000 | 0 | 5 | 5 | 5 |
| 133 | 250 | 0 | 4.5 | 5 | 5 |
| | 500 | 0 | 5 | 5 | 5 |
| | 1000 | 0 | 5 | 5 | 5 |
| 134 | 250 | 0 | 5 | 5 | 5 |
| | 500 | 0 | 5 | 5 | 5 |
| | 1000 | 0 | 5 | 5 | 5 |
| 135 | 250 | 0 | 5 | 5 | 5 |
| | 500 | 0 | 5 | 5 | 5 |
| | 1000 | 0.5 | 5 | 5 | 5 |
| 136 | 250 | 0 | 5 | 5 | 5 |
| | 500 | 0 | 5 | 5 | 5 |
| | 1000 | 0 | 5 | 5 | 5 |
| 137 | 250 | 0 | 5 | 5 | 5 |
| | 500 | 0 | 5 | 5 | 5 |
| | 1000 | 0 | 5 | 5 | 5 |
| 138 | 250 | 0 | 5 | 5 | 5 |
| | 500 | 0 | 5 | 5 | 5 |
| | 1000 | 0 | 5 | 5 | 5 |
| 139 | 250 | 0 | 5 | 5 | 5 |
| | 500 | 0 | 5 | 5 | 5 |
| | 1000 | 0 | 5 | 5 | 5 |
| 140 | 250 | 0 | 5 | 5 | 5 |
| | 500 | 0 | 5 | 5 | 5 |
| | 1000 | 1 | 5 | 5 | 5 |
| 141 | 250 | 0 | 4.5 | 5 | 5 |
| | 500 | 0 | 5 | 5 | 5 |
| | 1000 | 0 | 5 | 5 | 5 |
| 142 | 250 | 0 | 5 | 5 | 5 |
| | 500 | 0 | 5 | 5 | 5 |
| | 1000 | 0 | 5 | 5 | 5 |
| 144 | 250 | 0 | 5 | 2 | 5 |
| | 500 | 0 | 5 | 3 | 5 |
| | 1000 | 0 | 5 | 4 | 5 |
| 145 | 250 | 0 | 5 | 4 | 5 |
| | 500 | 0 | 5 | 5 | 5 |
| | 1000 | 1 | 5 | 5 | 5 |
| 146 | 250 | 0 | 5 | 5 | 5 |
| | 500 | 1 | 5 | 5 | 5 |
| | 1000 | 1 | 5 | 5 | 5 |
| 147 | 250 | 0 | 5 | 1 | 5 |
| | 500 | 1 | 5 | 2 | 5 |
| | 1000 | 1 | 5 | 3 | 5 |
| 149 | 250 | 0 | 5 | 4 | 5 |
| | 500 | 1 | 5 | 4.5 | 5 |
| | 1000 | 1.5 | 5 | 5 | 5 |
| 152 | 250 | 0 | 5 | 4.5 | 5 |
| | 500 | 0 | 5 | 5 | 5 |
| | 1000 | 0 | 5 | 5 | 5 |
| 154 | 250 | 0 | 4.5 | 4 | 5 |
| | 500 | 0 | 4.5 | 4.5 | 5 |
| | 1000 | 0 | 5 | 5 | 5 |
| 157 | 250 | 0 | 5 | 4 | 5 |
| | 500 | 0 | 5 | 5 | 5 |
| | 1000 | 0 | 5 | 5 | 5 |
| 161 | 250 | 0 | 5 | 4.5 | 5 |
| | 500 | 0 | 5 | 5 | 5 |
| | 1000 | 0 | 5 | 5 | 5 |
| 165 | 250 | 0 | 4.5 | 1 | 5 |
| | 500 | 0 | 5 | 3 | 5 |
| | 1000 | 0 | 5 | 4 | 5 |
| 166 | 250 | 0 | 5 | 5 | 5 |
| | 500 | 0 | 5 | 5 | 5 |
| | 1000 | 0 | 5 | 5 | 5 |
| 168 | 250 | 0 | 4.5 | 5 | 5 |
| | 500 | 0 | 5 | 5 | 5 |
| | 1000 | 1 | 5 | 5 | 5 |
| 169 | 250 | 0 | 4.5 | 5 | 5 |
| | 500 | 0 | 5 | 5 | 5 |
| | 1000 | 0 | 5 | 5 | 5 |
| 170 | 250 | 0 | 4 | 4 | 5 |
| | 500 | 0 | 4.5 | 4.5 | 5 |
| | 1000 | 0 | 5 | 4.5 | 5 |
| 171 | 250 | 0 | 4 | 4.5 | 5 |
| | 500 | 0 | 5 | 4.5 | 5 |
| | 1000 | 0 | 5 | 5 | 5 |
| 172 | 250 | 0 | 4.5 | 5 | 5 |
| | 500 | 0 | 4.5 | 5 | 5 |
| | 1000 | 0 | 5 | 5 | 5 |
| 174 | 250 | 0 | 4.5 | 5 | 5 |
| | 500 | 0 | 4.5 | 5 | 5 |
| | 1000 | 0 | 5 | 5 | 5 |
| 175 | 250 | 0 | 5 | 5 | 5 |
| | 500 | 0 | 5 | 5 | 5 |
| | 1000 | 1 | 5 | 5 | 5 |
| 176 | 250 | 0 | 3 | 4.5 | 4.5 |
| | 500 | 0 | 4 | 5 | 5 |
| | 1000 | 0 | 4.5 | 5 | 5 |
| 177 | 250 | 0 | 3 | 5 | 5 |
| | 500 | 0 | 4 | 5 | 5 |
| | 1000 | 0 | 5 | 5 | 5 |
| 178 | 250 | 0 | 4 | 5 | 5 |
| | 500 | 0 | 5 | 5 | 5 |
| | 1000 | 0 | 5 | 5 | 5 |
| 179 | 250 | 0 | 4.5 | 5 | 5 |
| | 500 | 0 | 5 | 5 | 5 |
| | 1000 | 0 | 5 | 5 | 5 |
| 180 | 250 | 0 | 5 | 5 | 5 |
| | 500 | 0 | 5 | 5 | 5 |
| | 1000 | 0 | 5 | 5 | 5 |
| 181 | 250 | 0 | 4 | 5 | 5 |
| | 500 | 0 | 4.5 | 5 | 5 |
| | 1000 | 0 | 5 | 5 | 5 |
| 182 | 250 | 0 | 5 | 5 | 5 |
| | 500 | 0 | 5 | 5 | 5 |
| | 1000 | 0 | 5 | 5 | 5 |
| 183 | 250 | 0 | 5 | 2 | 4.5 |
| | 500 | 0 | 5 | 3 | 4.5 |
| | 1000 | 0 | 5 | 4 | 5 |
| 184 | 250 | 4.5 | 5 | 5 | |
| | 500 | 0 | 4.5 | 5 | 5 |
| | 1000 | 0 | 5 | 5 | 5 |
| 185 | 250 | 0 | 5 | 5 | 5 |
| | 500 | 0 | 5 | 5 | 5 |
| | 1000 | 0 | 5 | 5 | 5 |
| 186 | 250 | 0 | 5 | 5 | 5 |
| | 500 | 0 | 5 | 5 | 5 |
| | 1000 | 0 | 5 | 5 | 5 |
| 187 | 250 | 0 | 5 | 5 | 5 |
| | 500 | 0 | 5 | 5 | 5 |
| | 1000 | 0 | 5 | 5 | 5 |
| 189 | 250 | 0 | 5 | 5 | 5 |
| | 500 | 0 | 5 | 5 | 5 |
| | 1000 | 0 | 5 | 5 | 5 |
| 190 | 250 | 0 | 4 | 5 | 5 |
| | 500 | 0 | 5 | 5 | 5 |
| | 1000 | 0 | 5 | 5 | 5 |
| 191 | 250 | 0 | 5 | 5 | 5 |
| | 500 | 0 | 5 | 5 | 5 |
| | 1000 | 0 | 5 | 5 | 5 |
| 192 | 250 | 0 | 5 | 5 | 5 |
| | 500 | 0 | 5 | 5 | 5 |
| | 1000 | 0 | 5 | 5 | 5 |
| 193 | 250 | 0 | 4.5 | 5 | 5 |
| | 500 | 0 | 4.5 | 5 | 5 |
| | 1000 | 0 | 5 | 5 | 5 |
| 194 | 250 | 0 | 5 | 5 | 5 |
| | 500 | 0 | 5 | 5 | 5 |

TABLE 3-continued

| Compound No. | Application Rate (g/10a) | Phytotoxicity to Rice | Herbicidal Effect | | |
|---|---|---|---|---|---|
| | | | Barnyard grass | Cyperaceous weed | Broadleak weed |
| | 1000 | 1 | 5 | 5 | 5 |
| | 250 | 0 | 5 | 5 | 5 |
| 195 | 500 | 0 | 5 | 5 | 5 |
| | 1000 | 1 | 5 | 5 | 5 |
| | 250 | 0 | 5 | 5 | 5 |
| 196 | 500 | 0 | 5 | 5 | 5 |
| | 1000 | 0 | 5 | 5 | 5 |
| | 250 | 0 | 4.5 | 5 | 5 |
| 197 | 500 | 0 | 4.5 | 5 | 5 |
| | 1000 | 0 | 5 | 5 | 5 |
| | 250 | 0 | 5 | 5 | 5 |
| 198 | 500 | 0 | 5 | 5 | 5 |
| | 1000 | 0 | 5 | 5 | 5 |
| | 250 | 0 | 5 | 5 | 5 |
| 199 | 500 | 0 | 5 | 5 | 5 |
| | 1000 | 0 | 5 | 5 | 5 |
| | 250 | 0 | 5 | 5 | 5 |
| 200 | 500 | 0 | 5 | 5 | 5 |
| | 1000 | 0 | 5 | 5 | 5 |
| | 250 | 0 | 5 | 5 | 5 |
| 201 | 500 | 0 | 5 | 5 | 5 |
| | 1000 | 0 | 5 | 5 | 5 |
| | 250 | 0 | 5 | 5 | 5 |
| 202 | 500 | 0 | 5 | 5 | 5 |
| | 1000 | 0 | 5 | 5 | 5 |
| | 250 | 0 | 4.5 | 5 | 5 |
| 203 | 500 | 0 | 5 | 5 | 5 |
| | 1000 | 0 | 5 | 5 | 5 |
| | 250 | 0 | 5 | 5 | 5 |
| 204 | 500 | 0 | 5 | 5 | 5 |
| | 1000 | 0 | 5 | 5 | 5 |
| | 250 | 0 | 5 | 5 | 5 |
| 205 | 500 | 0 | 5 | 5 | 5 |
| | 1000 | 0 | 5 | 5 | 5 |
| | 205 | 0 | 5 | 5 | 5 |
| 206 | 500 | 0 | 5 | 5 | 5 |
| | 1000 | 0 | 5 | 5 | 5 |
| | 62.5 | 0.5 | 2 | 1 | 4 |
| Simetryne* | 125 | 2 | 3 | 3 | 5 |
| | 250 | 5 | 5 | 5 | 5 |
| Untreated Area | — | 0 | 0 | 0 | 0 |

*Control Compound: 2,4-bis(ethylamino)-6-methylthio-1,3,5-triazine

EXPERIMENT 2

Polyethylene pots having a surface area of 1/5000 ares were filled with field soil (dry clayish loam) and seeded with seeds of rice plant, wheat, barnyard grass, radish and "Aobiyu" (Amaranthus retroflexus L.), covered with the same soil at a depth of one cm and placed in a green house to allow the plants to germinate. After germination and at 2-leaf stage for rice plant, 3-leaf stage for wheat and when the first leaf (following a pair of baby leaves) came out for radish and Aobiyu, the wettable powder formulated as in Example 1 was weighed in a predetermined amount and, after diluted with 2 ml of water per pot, sprayed thoroughly on the foliage of the weed plants. Two weeks after the treatment, the herbicidal activity and phytotoxicity against the useful plants were observed.

The results are shown in Table 4. The scale in the Table is the same as that in Experiment 1.

TABLE 4

| Compound No. | Compound concentration | Rice plant | Wheat | Barnyard grass | Radish | Aobiyu |
|---|---|---|---|---|---|---|
| | 0.25 | 0 | 0 | 0 | 5 | 5 |
| 1 | 0.5 | 2 | 1 | 2 | 5 | 5 |
| | 1 | 3 | 3 | 5 | 5 | 5 |
| | 0.25 | 0 | 0 | 2 | 5 | 5 |
| 4 | 0.5 | 0 | 1 | 2 | 5 | 5 |
| | 1 | 1 | 2 | 3 | 5 | 5 |
| | 0.25 | 0 | 0 | 4 | 5 | 5 |
| 8 | 0.5 | 1 | 3 | 4.5 | 5 | 5 |
| | 1 | 2 | 4 | 5 | 5 | 5 |
| | 0.25 | 0 | 0 | 2 | 5 | 5 |
| 10 | 0.5 | 1 | 2 | 4 | 5 | 5 |
| | 1 | 1 | 3 | 5 | 5 | 5 |
| | 0.25 | 0 | 0 | 4 | 1 | 1 |
| 19 | 0.5 | 0 | 0 | 5 | 3 | 4.5 |
| | 1 | 0.5 | 0 | 5 | 5 | 5 |
| | 0.25 | 0 | 0 | 1 | 3 | 4 |
| 24 | 0.5 | 0 | 0 | 2 | 4.5 | 5 |
| | 1 | 0 | 1 | 3 | 5 | 5 |
| | 0.25 | 0 | 0 | 2 | 5 | 5 |
| 27 | 0.5 | 0 | 0 | 5 | 5 | 5 |
| | 1 | 0 | 0.5 | 5 | 5 | 5 |
| | 0.25 | 0 | 0 | 2 | 2 | 3 |
| 34 | 0.5 | 0 | 0 | 5 | 4 | 4.5 |
| | 1 | 0 | 0 | 5 | 4.5 | 5 |
| | 0.25 | 0 | 0 | 1 | 1 | 1 |
| 36 | 0.5 | 0 | 0 | 4 | 3 | 3 |
| | 1 | 0 | 0 | 5 | 5 | 4.5 |
| | 0.25 | 0 | 0 | 3 | 3 | 3 |
| 38 | 0.5 | 0 | 0 | 4 | 4 | 4 |
| | 1 | 1 | 1 | 4.5 | 5 | 5 |
| | 0.25 | 0 | 0 | 4.5 | 5 | 5 |
| 41 | 0.5 | 2 | 2 | 5 | 5 | 5 |
| | 1 | 4 | 4 | 5 | 5 | 5 |
| | 0.25 | 0 | 0 | 2 | 5 | 5 |
| 43 | 0.5 | 1 | 1 | 3 | 5 | 5 |
| | 1 | 2 | 2 | 5 | 5 | 5 |
| | 0.25 | 0 | 0 | 2 | 4.5 | 4 |
| 46 | 0.5 | 0 | 0 | 3 | 5 | 5 |
| | 1 | 0 | 0 | 4 | 5 | 5 |
| | 0.25 | 0 | 0 | 4.5 | 5 | 5 |
| 47 | 0.5 | 0 | 0 | 5 | 5 | 5 |
| | 1 | 0 | 2 | 5 | 5 | 5 |
| | 0.25 | 0 | 0 | 3 | 4 | 4 |
| 54 | 0.5 | 0 | 0 | 5 | 4.5 | 5 |
| | 1 | 1 | 1 | 5 | 5 | 5 |
| | 0.25 | 0 | 0 | 5 | 4.5 | 5 |
| 58 | 0.5 | 0 | 0 | 5 | 5 | 5 |
| | 1 | 1 | 2 | 5 | 5 | 5 |
| | 0.25 | 0 | 0 | 3 | 4 | 5 |
| 63 | 0.5 | 0 | 1 | 4 | 5 | 5 |
| | 1 | 1 | 2 | 5 | 5 | 5 |
| | 0.25 | 0 | 0 | 3 | 1 | 1 |
| 66 | 0.5 | 0 | 0 | 4 | 4 | 3 |
| | 1 | 0 | 0 | 5 | 5 | 5 |
| | 0.25 | 0 | 0 | 1 | 4 | 5 |
| 67 | 0.5 | 0 | 0 | 3 | 4.5 | 5 |
| | 1 | 0 | 1 | 4 | 5 | 5 |
| | 0.25 | 0 | 0 | 4 | 5 | 5 |
| 68 | 0.5 | 1 | 1 | 5 | 5 | 5 |
| | 1 | 2 | 2 | 5 | 5 | 5 |
| | 0.25 | 0 | 0 | 4 | 3 | 3 |
| 69 | 0.5 | 0 | 0 | 5 | 4.5 | 4 |
| | 1 | 1 | 2 | 5 | 5 | 5 |
| | 0.25 | 0 | 0 | 4 | 5 | 5 |
| 76 | 0.5 | 0 | 1 | 5 | 5 | 5 |
| | 1 | 1 | 2 | 5 | 5 | 5 |
| | 0.25 | 0 | 0 | 2 | 4.5 | 5 |
| 78 | 0.5 | 0 | 1 | 4 | 5 | 5 |
| | 1 | 1 | 1 | 5 | 5 | 5 |
| | 0.25 | 0 | 0 | 4 | 4.5 | 4.5 |
| 80 | 0.5 | 0 | 1 | 5 | 5 | 5 |
| | 1 | 1 | 2 | 5 | 5 | 5 |
| | 0.25 | 2 | 0 | 3 | 5 | 5 |
| 85 | 0.5 | 3 | 1 | 4 | 5 | 5 |
| | 1 | 4 | 2 | 5 | 5 | 5 |
| | 0.25 | 0 | 0 | 5 | 5 | 5 |
| 86 | 0.5 | 1 | 2 | 5 | 5 | 5 |
| | 1 | 2 | 3 | 5 | 5 | 5 |
| | 0.25 | 0 | 0 | 3 | 3 | 4 |
| 89 | 0.5 | 0 | 1 | 4 | 3 | 5 |

TABLE 4-continued

| Compound No. | Compound concentration | Rice plant | Wheat | Barnyard grass | Radish | Aobiyu |
|---|---|---|---|---|---|---|
| | 1 | 1 | 2 | 5 | 5 | 5 |
| | 0.25 | 0 | 0 | 3 | 2 | 5 |
| 92 | 0.5 | 1 | 1 | 4.5 | 3 | 5 |
| | 1 | 1 | 3 | 5 | 5 | 5 |
| | 0.25 | 0 | 0 | 4.5 | 5 | 5 |
| 94 | 0.5 | 1 | 2 | 5 | 5 | 5 |
| | 1 | 2 | 3 | 5 | 5 | 5 |
| | 0.25 | 0 | 0 | 4.5 | 5 | 5 |
| 101 | 0.5 | 0 | 1 | 5 | 5 | 5 |
| | 1 | 2 | 2 | 5 | 5 | 5 |
| | 0.25 | 0 | 0 | 3 | 3 | 5 |
| 106 | 0.5 | 0 | 1 | 4 | 4 | 5 |
| | 1 | 0 | 3 | 5 | 5 | 5 |
| | 0.25 | 0 | 0 | 4 | 5 | 5 |
| 109 | 0.5 | 0 | 1 | 5 | 5 | 5 |
| | 1 | 1 | 3 | 5 | 5 | 5 |
| | 0.25 | 0 | 0 | 2 | 3 | 4 |
| 113 | 0.5 | 0 | 1 | 4 | 4 | 5 |
| | 1 | 1 | 2 | 5 | 5 | 5 |
| | 0.25 | 0 | 0 | 3 | 3 | 4.5 |
| 114 | 0.4 | 0 | 0 | 4.5 | 4.5 | 5 |
| | 1 | 1 | 1 | 5 | 5 | 5 |
| | 0.25 | 2 | 1 | 5 | 5 | 5 |
| 115 | 0.5 | 3 | 2 | 5 | 5 | 5 |
| | 1 | 4 | 4 | 5 | 5 | 5 |
| | 0.25 | 0 | 0 | 4.5 | 5 | 5 |
| 117 | 0.5 | 0 | 0 | 5 | 5 | 5 |
| | 1 | 1 | 2 | 5 | 5 | 5 |
| | 0.25 | 0 | 2 | 5 | 5 | 5 |
| 122 | 0.5 | 1 | 3 | 5 | 5 | 5 |
| | 1 | 3 | 3 | 5 | 5 | 5 |
| | 0.25 | 0 | 0 | 4 | 5 | 5 |
| 125 | 0.5 | 1 | 1 | 5 | 5 | 5 |
| | 1 | 2 | 3 | 5 | 5 | 5 |
| | 0.25 | 0 | 0 | 3 | 4 | 5 |
| 126 | 0.5 | 0 | 1 | 4 | 4.5 | 5 |
| | 1 | 1 | 2 | 5 | 5 | 5 |
| | 0.25 | 0 | 0 | 4 | 5 | 4.5 |
| 129 | 0.5 | 0 | 1 | 5 | 5 | 5 |
| | 1 | 2 | 3 | 5 | 5 | 5 |
| | 0.25 | 0 | 0 | 4.5 | 5 | 5 |
| 135 | 0.5 | 0 | 0 | 5 | 5 | 5 |
| | 1 | 1 | 2 | 5 | 5 | 5 |
| | 0.25 | 0 | 0 | 4.5 | 5 | 5 |
| 139 | 0.5 | 0 | 0 | 5 | 5 | 5 |
| | 1 | 2 | 3 | 5 | 5 | 5 |
| | 0.25 | 1 | 0 | 4.5 | 5 | 5 |
| 144 | 0.5 | 2 | 1 | 5 | 5 | 5 |
| | 1 | 4 | 3 | 5 | 5 | 5 |
| | 0.25 | 0 | 0 | 5 | 5 | 5 |
| 145 | 0.5 | 1 | 2 | 5 | 5 | 5 |
| | 1 | 2 | 3 | 5 | 5 | 5 |
| | 0.25 | 0 | 2 | 5 | 5 | 5 |
| 149 | 0.5 | 1 | 2 | 5 | 5 | 5 |
| | 1 | 3 | 4 | 5 | 5 | 5 |
| | 0.25 | 0 | 1 | 4.5 | 5 | 4.5 |
| 152 | 0.5 | 0 | 1 | 5 | 5 | 5 |
| | 1 | 1 | 3 | 5 | 5 | 5 |
| | 0.25 | 0 | 0 | 4 | 4 | 5 |
| 157 | 0.5 | 1 | 1 | 5 | 5 | 5 |
| | 1 | 2 | 3 | 5 | 5 | 5 |
| | 0.25 | 0 | 0 | 4 | 4.5 | 5 |
| 161 | 0.5 | 1 | 1 | 5 | 5 | 5 |
| | 1 | 2 | 2 | 5 | 5 | 5 |
| | 0.25 | 0 | 0 | 5 | 4.5 | 5 |
| 165 | 0.5 | 0 | 1 | 5 | 5 | 5 |
| | 1 | 2 | 3 | 5 | 5 | 5 |
| | 0.25 | 1 | 1 | 4 | 5 | 4.5 |
| 168 | 0.5 | 2 | 2 | 5 | 5 | 5 |
| | 1 | 2 | 3 | 5 | 5 | 5 |
| | 0.25 | 0 | 1 | 4.5 | 5 | 5 |
| 169 | 0.5 | 1 | 3 | 5 | 5 | 5 |
| | 1 | 2 | 4 | 5 | 5 | 5 |
| | 0.25 | 0 | 0 | 3 | 1 | 2 |
| 171 | 0.5 | 0 | 0 | 4 | 2 | 4 |
| | 1 | 0 | 1 | 5 | 4 | 5 |
| | 0.25 | 0 | 1 | 4 | 4.5 | 5 |
| 172 | 0.5 | 1 | 2 | 4.5 | 5 | 5 |
| | 1 | 2 | 2 | 5 | 5 | 5 |
| | 0.25 | 0 | 0 | 4 | 4.5 | 4 |
| 178 | 0.5 | 0 | 1 | 5 | 5 | 5 |
| | 1 | 2 | 2 | 5 | 5 | 5 |
| | 0.25 | 0 | 0 | 4.5 | 4.5 | 4 |
| 180 | 0.5 | 0 | 2 | 5 | 5 | 5 |
| | 1 | 2 | 3 | 5 | 5 | 5 |
| | 0.25 | 0 | 0 | 4 | 5 | 5 |
| 182 | 0.5 | 0 | 1 | 5 | 5 | 5 |
| | 1 | 2 | 3 | 5 | 5 | 5 |
| | 0.25 | 0 | 0 | 3 | 2 | 2 |
| 184 | 0.5 | 0 | 0 | 4 | 4 | 4 |
| | 1 | 1 | 2 | 5 | 5 | 5 |
| | 0.25 | 0 | 0 | 4 | 4.5 | 4.5 |
| 185 | 0.5 | 1 | 2 | 5 | 5 | 5 |
| | 1 | 2 | 3 | 5 | 5 | 5 |
| | 0.25 | 0 | 1 | 4 | 5 | 5 |
| 186 | 0.5 | 1 | 2 | 5 | 5 | 5 |
| | 1 | 3 | 4 | 5 | 5 | 5 |
| | 0.25 | 2 | 2 | 5 | 5 | 5 |
| 189 | 0.5 | 3 | 2 | 5 | 5 | 5 |
| | 1 | 4 | 4 | 5 | 5 | 5 |
| | 0.25 | 0 | 1 | 4 | 5 | 4.5 |
| 193 | 0.5 | 1 | 2 | 5 | 5 | 5 |
| | 1 | 3 | 4 | 5 | 5 | 5 |
| | 0.25 | 0 | 0 | 5 | 5 | 4 |
| 200 | 0.5 | 1 | 2 | 5 | 5 | 5 |
| | 1 | 2 | 3 | 5 | 5 | 5 |
| | 0.25 | 0 | 1 | 3 | 4.5 | 4.5 |
| 203 | 0.5 | 1 | 2 | 4 | 5 | 5 |
| | 1 | 3 | 4 | 5 | 5 | 5 |
| Untreated Area | — | 0 | 0 | 0 | 0 | 0 |

What is claimed is:

1. A compound represented by the formula

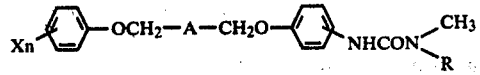

wherein X is a halogen, an alkyl or trifluoromethyl, n is an integer of from 0 to 3, provided that when n is 2 or 3, X may be different to each other; A is

or —C≡C—, wherein

is in trans form; and R is methyl or methoxy.

2. A compound according to claim 1 wherein X is a halogen, an alkyl or trifluoromethyl, n is an integer of from 0 to 3, provided that when n is 2 or 3, X may be different to each other; A is

in trans form; and R is methyl.

3. A compound according to claim 1 wherein X is a halogen; n is an integer of from 0 to 3; A is

in trans form; and R is methyl.

4. A compound according to claim 1 wherein X is an alkyl; n is an integer of from 0 to 3; A is

in trans form; and R is methyl.

5. A compound according to claim 1 wherein X is trifluoromethyl; n is an integer of from 0 to 3; A is

in trans form; and R is methyl.

6. A compound according to claim 1 wherein X is a halogen, an alkyl or trifluoromethyl, n is an integer of from 0 to 3, provided that when n is 2 or 3, X may be different to each other; A is

in trans form; and R is methoxy.

7. A compound according to claim 1 wherein X is a halogen; n is an integer of from 0 to 3; A is

in trans form; and R is methoxy.

8. A compound according to claim 1 wherein X is an alkyl; n is an integer of from 0 to 3; A is

in trans form; and R is methoxy.

9. A compound according to claim 1 wherein X is trifluoromethyl, n is an integer of from 0 to 3; A is

in trans form; and R is methoxy.

10. A compound according to claim 1 wherein X is a halogen, an alkyl or trifluoromethyl; n is an integer of from 0 to 3, provided that when n is 2 or 3, X may be different to each other; A is —C≡C—; and R is methyl.

11. A compound according to claim 1 wherein X is a halogen; n is an integer of from 0 to 3; A is —C≡C—; and R is methyl.

12. A compound according to claim 1 wherein X is an alkyl; n is an integer of from 0 to 3; A is —C≡C—; and R is methyl.

13. A compound according to claim 1 wherein X is trifluoromethyl; n is an integer of from 0 to 3, A is —C≡C—; and R is methyl.

14. A compound according to claim 1 wherein X is a halogen, an alkyl or trifluoromethyl, n is an integer of from 0 to 3, provided that when n is 2 or 3, X may be different to each other; A is —C≡C—; and R is methoxy.

15. A compound according to claim 1 wherein X is a halogen; n is an integer of from 0 to 3; A is —C≡C—; and R is methoxy.

16. A compound according to claim 1 wherein X is an alkyl; n is an integer of from 0 to 3; A is —C≡C—; and R is methoxy.

17. A compound according to claim 1 wherein X is a halogen, an alkyl or trifluoromethyl, n is an integer of from 0 to 3; A is —C≡C—; and R is methoxy.

18. A highly selective herbicidal composition comprising a carrier and a herbicidally effective amount of a compound represented by the formula

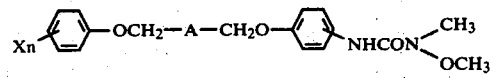

wherein X is a halogen, an alkyl or trifluoromethyl, n is an integer of from 0 to 3, provided that when n is 2 or 3, X may be different to each other; and A is

or —C≡C—, wherein

is in trans form.

19. A composition according to claim 18 wherein the form of said composition is selected from the group consisting of wettable powder, emulsifiable concentrate, granule, dust and tablet.

* * * * *